US010842429B2

(12) United States Patent
Kinnunen et al.

(10) Patent No.: US 10,842,429 B2
(45) Date of Patent: Nov. 24, 2020

(54) METHOD AND SYSTEM FOR ASSESSING A READINESS SCORE OF A USER

(71) Applicant: Oura Health Oy, Oulu (FI)

(72) Inventors: Hannu Kinnunen, Oulu (FI); Harri Laakkonen, Oulu (FI); Kari Kivelä, Helsinki (FI); Ashley Colley, Rovaniemi (FI); Petteri Lahtela, Jääli (FI); Markku Koskela, Oulu (FI); Heidi Jurvelin, Oulu (FI)

(73) Assignee: Oura Health Oy, Oulu (FI)

( * ) Notice: Subject to any disclaimer, the term of this patent is extended or adjusted under 35 U.S.C. 154(b) by 272 days.

(21) Appl. No.: 15/551,632

(22) PCT Filed: Feb. 23, 2016

(86) PCT No.: PCT/FI2016/050113
§ 371 (c)(1),
(2) Date: Aug. 17, 2017

(87) PCT Pub. No.: WO2016/135382
PCT Pub. Date: Sep. 1, 2016

(65) Prior Publication Data
US 2018/0042540 A1 Feb. 15, 2018

Related U.S. Application Data

(60) Provisional application No. 62/121,425, filed on Feb. 26, 2015, provisional application No. 62/205,114, (Continued)

(51) Int. Cl.
*A61B 5/00* (2006.01)
*A61B 5/16* (2006.01)
(Continued)

(52) U.S. Cl.
CPC ............... *A61B 5/16* (2013.01); *A61B 5/01* (2013.01); *A61B 5/02405* (2013.01);
(Continued)

(58) Field of Classification Search
CPC ... A61B 5/0002; A61B 5/0004; A61B 5/0006; A61B 5/0008; A61B 5/01; A61B 5/02;
(Continued)

(56) References Cited

U.S. PATENT DOCUMENTS

| 2005/0080344 A1* | 4/2005 | Nishii | ...................... A61B 5/02 600/483 |
| 2010/0168531 A1 | 7/2010 | Shaltis et al. | |

(Continued)

FOREIGN PATENT DOCUMENTS

| JP | 2007222276 A | 9/2007 |
| WO | 2013161072 A1 | 10/2013 |

OTHER PUBLICATIONS

Jones A Y Me et al: "Activity Levels and Resting Energy Expenditure in an Elderly Population: A Pilot Study", Hong Kong Physiotherapy Journal, Elsevier, Amsterdam, NL, vol. 22, No. 1, Jan. 1, 2004, ISSN: 1013-7025(09)70047-8, 4 pages.
(Continued)

*Primary Examiner* — Eugene T Wu
(74) *Attorney, Agent, or Firm* — Ziegler IP Law Group, LLC

(57) ABSTRACT

A method and a system for assessing readiness of a user, the method including obtaining the user's movements; using the obtained user's movements to determine a nature of the period, wherein the nature of the period is selected from an activity period and a rest period; measuring at least one biosignal of the user during the rest period; determining a rest summary for the rest period, based on the measured at least one biosignal and at least one biosignal of a previous
(Continued)

rest period; determining an activity summary for the activity period, based on the obtained movements of an activity period and obtained movements of at least one previous activity period; determining a body response summary based on the rest summary and the activity summary; and calculating a readiness score based on the body response summary and a previous body response summary, whereby the readiness score indicates a level of readiness of the user.

13 Claims, 14 Drawing Sheets

Related U.S. Application Data filed on Aug. 14, 2015, provisional application No. 62/260,760, filed on Nov. 30, 2015.

(51) Int. Cl.
| | | |
|---|---|---|
| *A61B 5/01* | (2006.01) | |
| *A61B 5/024* | (2006.01) | |
| *A61B 5/0404* | (2006.01) | |
| *A61B 5/11* | (2006.01) | |
| *G06F 19/00* | (2018.01) | |
| *A61B 5/0496* | (2006.01) | |
| *A61B 5/0488* | (2006.01) | |

(52) U.S. Cl.
CPC ........ *A61B 5/02433* (2013.01); *A61B 5/0404* (2013.01); *A61B 5/1116* (2013.01); *A61B 5/1118* (2013.01); *A61B 5/4806* (2013.01); *A61B 5/4809* (2013.01); *A61B 5/6802* (2013.01); *A61B 5/6826* (2013.01); *A61B 5/7271* (2013.01); *G06F 19/3481* (2013.01); *A61B 5/0022* (2013.01); *A61B 5/0024* (2013.01); *A61B 5/0488* (2013.01); *A61B 5/0496* (2013.01); *A61B 5/165* (2013.01); *A61B 5/7264* (2013.01); *A61B 5/7275* (2013.01); *A61B 5/742* (2013.01); *A61B 2562/0219* (2013.01); *A61B 2562/0223* (2013.01)

(58) Field of Classification Search
CPC ......... A61B 5/0205; A61B 5/16; A61B 5/165; A61B 5/168; A61B 5/4806; A61B 5/4809; A61B 5/4812; A61B 5/4815; A61B 5/6826; A61B 5/7271; A61B 5/7275; A61B 5/74; A61B 5/742
See application file for complete search history.

(56) References Cited

U.S. PATENT DOCUMENTS

| | | | | |
|---|---|---|---|---|
| 2014/0073486 | A1* | 3/2014 | Ahmed | A61B 5/02405 482/9 |
| 2015/0119732 | A1* | 4/2015 | Wisbey | A61B 5/02405 600/508 |
| 2015/0127265 | A1* | 5/2015 | Iizuka | G06F 19/3481 702/19 |
| 2015/0182129 | A1* | 7/2015 | Colley | A61B 5/0205 600/301 |

OTHER PUBLICATIONS

Rennie K et al: "A Combined Heart Rate and Movemetn Sensor: Proof of Concept and Preliminary Testing Study", European Journal of Clinical Nutirition, vol. 54, No. 5, May 1, 2000, DOI: 10.1038/SJ.EJCN.1600973, 6 pages.

International Search Report, Application No. PCT/FI2016/050113, dated May 26, 2016, 3 pages.

* cited by examiner

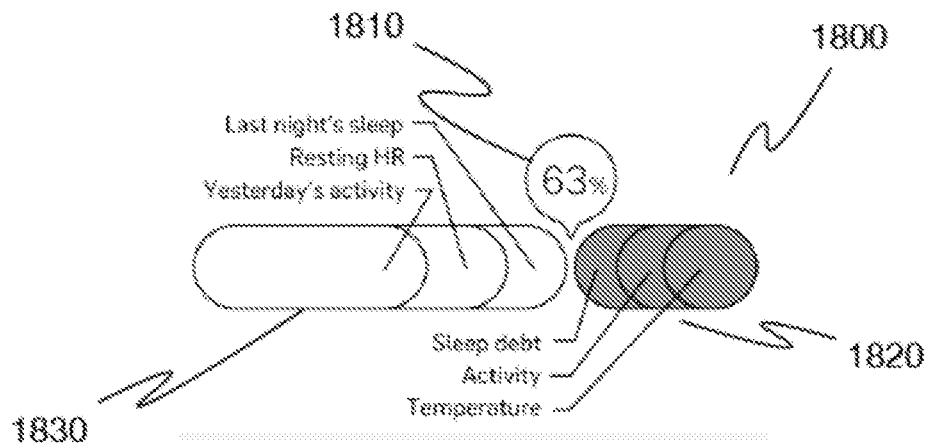
FIG. 18A
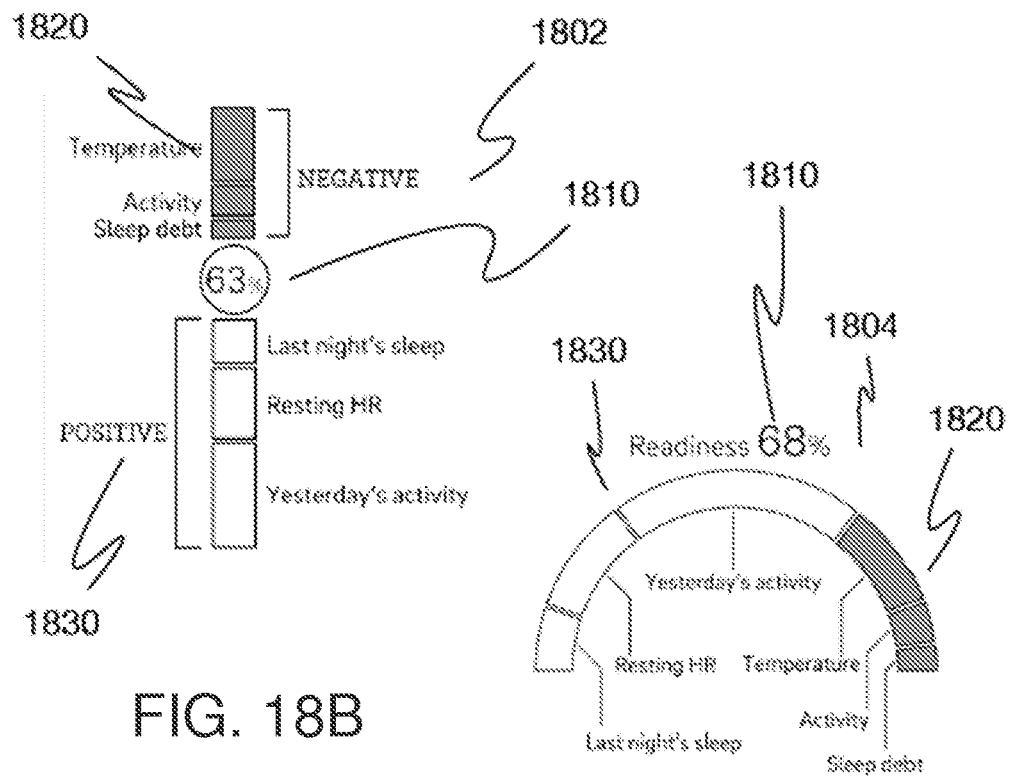
FIG. 18B
FIG. 18C

METHOD AND SYSTEM FOR ASSESSING A READINESS SCORE OF A USER

TECHNICAL FIELD

The present disclosure generally relates to analysing and processing data related to physical activities and biological signals of an individual, and, more specifically, to a method and a system for assessing readiness score of a user.

BACKGROUND

An individual is subjected to various kinds of mental and physical loads in a day to day life. For example, an individual may be subjected to physical loads (such as physical exercise, walking, driving, playing and the like) and mental loads (such as inappropriate sleep, inappropriate rest, stress and the like). Further, if such mental and physical loads are not managed or handled efficiently, it may induce mental and physical stresses. For example, the physical stress may cause health issues such as backache, spine problems and the like, and the mental stress may cause reduction in sleep, hinder concentration and impair motivation. Therefore, it is important to analyse how an individual manages or handles such mental and physical loads for maintaining a good physical and mental health and what is the readiness of the individual to face further challenges.

Conventionally, there are devices that may calculate biological signals of an individual and monitor physical activities of the individual. However, such devices do not provide any information which relates to recovery of the individual from mental or physical loads that the individual is subjected to, neither do they provide any information related to a readiness score of the individual. Further, such devices do not analyse data, associated with health parameters of the individual, in detail. For example, such devices do not consider the individuals' historical data. Also, such devices are not capable of providing appropriate suggestions or recommendations that may help the individual to efficiently recover from such mental and/or physical load and to increase the readiness score.

Therefore, in light of the foregoing discussion, there exists a need to overcome the aforementioned drawbacks of assessing readiness score of the user.

SUMMARY

The present disclosure seeks to provide a method for assessing readiness score of a user.

The present disclosure also seeks to provide a system for assessing readiness score of a user.

In one aspect, an embodiment of the present disclosure provides a method for assessing readiness score of a user. The method comprises:
  obtaining the user's movements;
  using the obtained user's movements to determine a nature of the period, wherein the nature of the period is selected from an activity period and a rest period;
  measuring at least one biosignal of the user during the rest period;
  determining a rest summary for the rest period, based on the measured at least one biosignal and at least one biosignal of a previous rest period;
  determining an activity summary for the activity period, based on the obtained movements of an activity period and obtained movements of at least one previous activity period;
  determining a body response summary based on the rest summary and the activity summary; and
  calculating a readiness score based on the body response summary and a previous body response summary, whereby the readiness score indicates a level of readiness of the user.

In another aspect, an embodiment of the present disclosure provides a system for assessing readiness score of a user. The system comprises
  a ring configured to be worn by the user and comprising means for measuring at least one biosignal of the user during a rest period,
  a mobile communication device configured to communicate with the ring,
  means for measuring user's movements during an activity period and the rest period, and
  a server configured to communicate with the mobile communication device, the server being operable to
    use the measured user's movements to determine a nature of the period, wherein the nature of the period is selected from the activity period and the rest period,
    determine a rest summary for the rest period, based on the measured at least one biosignal and at least one biosignal of a previous rest period,
    determine an activity summary for the activity period, based on the measured movements and measured movements of at least one previous activity period,
    determine a body response summary based on the rest summary and the activity summary; and
    calculate a readiness score based on the body response summary and a previous body response summary, whereby the readiness score indicates a level of readiness of the user.

Embodiments of the present disclosure substantially eliminate or at least partially address the aforementioned problems in the prior art, by calculating a readiness score of a user and by providing appropriate instructions to improve the readiness score.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIG. 18A, 18B, 18C are illustrations of exemplary user interfaces according to embodiments of the present disclosure.

Figure 1:
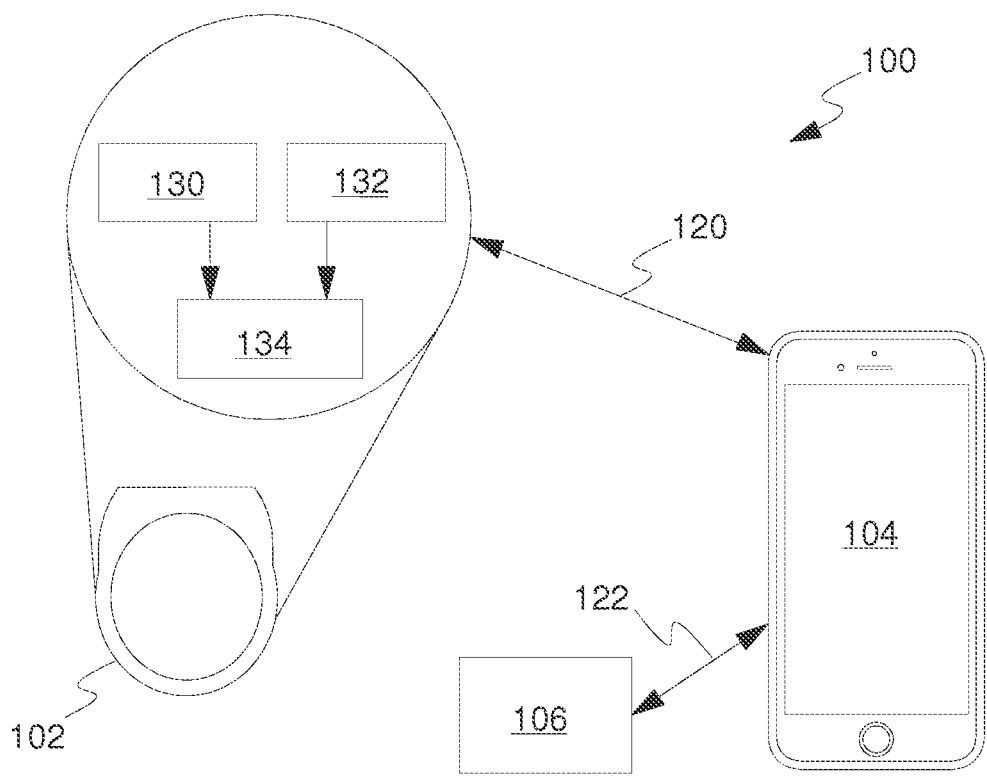
FIG. 1 is a schematic illustration of a system for assessing readiness score of a user, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method for assessing readiness score of a user. The method comprises:

obtaining the user's movements;

using the obtained user's movements to determine a nature of the period, wherein the nature of the period is selected from an activity period and a rest period;

measuring at least one biosignal of the user during the rest period;

determining a rest summary for the rest period, based on the measured at least one biosignal and at least one biosignal of a previous rest period;

determining an activity summary for the activity period, based on the obtained movements of an activity period and obtained movements of at least one previous activity period;

determining a body response summary based on the rest summary and the activity summary; and calculating a readiness score based on the body response summary and a previous body response summary, whereby the readiness score indicates a level of readiness of the user.

In another aspect, an embodiment of the present disclosure provides a system for assessing readiness score of a user. The system comprises:

a ring configured to be worn by the user and comprising means for measuring at least one biosignal of the user during a rest period, a mobile communication device configured to communicate with the ring, means for measuring user's movements during an activity period and the rest period, and a server configured to communicate with the mobile communication device, the server being operable to use the measured user's movements to determine a nature of the period, wherein the nature of the period is selected from the activity period and the rest period, determine a rest summary for the rest period, based on the measured at least one biosignal and at least one biosignal of a previous rest period, determine an activity summary for the activity period, based on the measured movements and measured movements of at least one previous activity period, determine a body response summary based on the rest summary and the activity summary; and calculate a readiness score based on the body response summary and a previous body response summary, whereby the readiness score indicates a level of readiness of the user.

The term readiness in this description encompasses not only alertness or readiness of the user, or the lack of alertness or readiness of the user, but also physical and mental recovery from various kinds of stress. The readiness score is an estimated readiness of the user to perform well at a given day. It summarizes both physical and mental prerequisites for a good day. In essence, it covers the effects of earlier physical activity, previous night's sleep, and body responses measured lately. Body responses can mean for instance temperature, resting heart rates relative to user's own normative values, or how much they have changed as a response to previous day's physical activity. The terms recovery, alertness and readiness can be used interchangeably in this description and are meant to be understood as stated above.

The present method may use different calculation parameters and it is preferably designed to learn from previous measurements. For example, the method and device may take into account the data from previous week, two weeks, a month or two months (or any other time lapse), in order to set personalized calibrations, averages and/or limits, that are typical to the user. The device may also comprise a means for resetting all measurements and calculations. Such personalized settings can be used to give further instructions to the user, to improve the user's life balance. Indeed, different users may have different reactions to stress and illnesses, as well as different means to cope and recover from stress. Furthermore, the gathered data could be used for varying the weight that is given to different aspects measured or obtained by the user, in order to further personalize the device.

In an embodiment, the ring of the system is configured to be suitably worn at a finger, such as an index finger, of the user. However, it may be evident to those skilled in the art that the system may be associated with other wearable devices, such as a device adapted to be worn at a wrist of the user. For example, the device may have the form of a ring and may be configured to have a size that is large enough to be suitably worn at the wrist of the user. According to a further embodiment, the ring is as described in PCT/FI2014/000043, which application is hereby incorporated by reference.

The ring or other device is configured to measure at least one biosignal of the user, and optionally the user's movements, which may be referred to as 'raw data' associated with the user. Further, the measured data is associated with the activity period and the rest period, as may be relevant. The term 'activity period' used herein refers to those periods of a day when the user is subjected to any physical activity, such as when the user is exercising, walking, playing or attending to normal day to day tasks. Further, the term 'rest period' used herein primarily relates to a sleeping period of the user in a day. However, the rest period may also include time period when the user is sitting or lying down to relax. The movements of the user are measured or obtained from a separate device, and used to determine whether the user is active or resting, i.e. to select the nature of the period.

In the present description, the step of measuring or obtaining the user's movements provides movement data and the measuring of at least one biosignal provides biosignal or biosignal data (which terms can be used interchangeably). The obtained movement data of the user during the rest period can be used for various purposes. For example, it is typically used to determine whether a moment of time belongs to the activity period or the rest period or possibly a further type of period if one or more such further types of period(s) have been defined. Further, it can be used as part of the starting data for determining the rest summary. A biosignal or several biosignals is determined during a rest period, but may be also determined during an activity period. For example, in case the temperature of the user is elevated during a rest period, it may be continued to be monitored during a following activity period, in order to ensure whether the increase was due to fever or another reason. Furthermore, elevated temperature readings such as fever can be programmed to adjust the readiness over an extended period of time, i.e. not only the following day. In practice, after being sick one or more days it will be beneficial to take additional easy days proportional to the length of the sickness.

According to an embodiment, the step of obtaining the user's movements is performed by measuring the user's movements or by retrieving the user's movement data from a separate device. The user's movements can comprise for example actual movements such as raising an arm or a hand, walking, running etc, or accumulated steps, an active time or a distance covered by the user.

Typically, the movements are measured by means for measuring the user's movements. These means can be arranged on the ring or other similar device to be worn, or in a mobile communication device or in a separate device destined to measure a user's movements, such as a pedometer. In one embodiment, the means for measuring user's movements is selected from the group consisting of an accelerometer, a gyroscope and a magnetic field sensor. It is further to be noted that the means for measuring the user's movements during the rest period can be the same means or different means from those used for measuring the user's movements during the activity period. For example, it is possible to use the measured biosignal for determining the movement data for the rest period.

According to an embodiment, the method further comprises measuring at least one biosignal during the activity period. According to another embodiment, the at least one biosignal (for either the rest period or the activity period) is selected from the group consisting of an electrocardiogram (EKG or ECG), a photoplethysmogram (PPG), an electromyogram (EMG), an electroocylogram (EOG), a heart rate, a heart rate variability, body temperature, a resting heart rate, an average heart rate and signals related to breathing. When a biosignal is measured both during activity and rest, it can be the same or different.

According to a further embodiment, determining the rest summary comprises at least one of determining a hypnogram, determining a sleep balance, determining lowest body temperature during rest and determining a resting heart rate. A hypnogram can be determined up to a certain accuracy with only motion data, although REM-sleep is rather difficult to differentiate from light sleep without a biosignal such as breathing rate and its dynamics, heart beat intervals or amplitude variation in ECG or PPG signal. Other possibilities are EMG, EEG or EOG that are part of polysomnographic measurement used in clinical sleep tests. On the other hand, it is also possible to use only PPG data to derive much of the same movement information than is needed regarding motion data, thus an accelerometer or other movement sensor is not mandatory. A movement sensor can be used to measure some additional information about the posture of the user, for example, but a PPG is typically sufficient to detect most of the movements. Regarding rest time related factors behind recovery/readiness, an alternative of a hypnogram would also be to determine parameters that are associated with deep sleep (for physical recovery) and REM sleep (for mental or cognitive recovery). This means determining how mentally rewarding the sleep was, and how physically rewarding the sleep was without use of a hypnogram. Use of a hypnogram could be beneficial in validating the determination, but there are alternative intermediate parameters that could also be used, such as breathing inconsistency, respiratory effort related parameters calculated from heart beat intervals or PPG pulse amplitude parameters, heart rate dynamics or stability of the parameters, eye motions, and so on. In the following, the general term "sleep factor" is used to encompass hypnograms as well as its alternatives as mentioned above.

Heart rate is one possible biosignal measured by the device in question. The heart rate is thus one optional, additional feature derivable from a PPG signal or an ECG signal. Further on, changes around the local mean or difference from whole night mean are more sensitive to sleep phases than the heart rate or the heart beat interval itself. The dynamics of PPG signal amplitude (e.g. difference between local max and local min around each heart beat pulse) or R peak amplitude (from ECG) provide approximately the same information as heart beat interval dynamics.

In a further embodiment, the heart rate is measured by means for measuring a heart rate, which comprise a photon source arranged on the inner surface of the ring and a photon detector arranged on the inner surface of the ring. In yet another embodiment, the ring further comprises a first electrode and a second electrode adapted to measure an electrocardiogram.

In one embodiment, the ring thus includes at least one motion sensor, such an accelerometer, a gyroscope, a magnetic field sensor or a combination thereof, to measure user's movement. The motion sensor is configured to generate motion data that is indicative of the movements of the user. For example, the motion sensor may be configured to determine linear motion information, rotational motion information, and the like. Further, such information (linear motion or rotational motion) may be combined or correlated to generate the motion data that is indicative of the user's movement. As mentioned above, the movement data can also be generated by a separate device and retrieved or obtained by the ring or the server.

In one embodiment, the heart rate is measured by measuring blood volume pulse. Specifically, the heart rate is determined by measuring PPG (photoplethysmogram) from the blood volume pulse. The PPG can be measured using optical electronics, particularity using the principle of transmittance or reflectance of light. For example, the ring includes optical electronics, i.e. at least one photon source and at least one photon detector positioned on an inner surface of the ring. The at least one photon source is infrared light (IR) emitting diode and the at least one photon detector is IR receiving diode (such as photon diode or photon transistor).

In an embodiment, when the ring is worn at the user's finger the optical electronics thereof acquire appropriate measurement data or biosignal data (i.e. blood volume pulse). Specifically, an IR light pulse is sent from the at least one photon source and thereafter the reflected IR light is received by the at least one photon detector. Further, the variations in volume of the blood vessels (during the flow of blood) result in variation in the measured transmission (i.e. IR light intensity) which is measured and processed to generate the PPG. Further, from a PPG waveform an inter-beat-interval i.e. a heart rate (time between two beats) is determined. Body temperature of the user is typically measured using a sensor for measuring temperature comprised in the device, for example a thermometer included in the ring.

The ring may also include other electronic components apart from the motion sensor and the optical electronics. Specifically, the ring is configured to collect and analyse the raw data (i.e. data of the motion sensor and the optical electronics). For example, the ring may include other electronic components which may include but not limited to a controller, a microprocessor, a memory and a communication module. The controller is operable to control operation of the motion sensor and the optical electronics for generating data related to the user's movement and the heart rate. The microprocessor may be operable to process or analyse the raw data generated by the motion sensor and the optical electronics. Further, the memory is used for storing the analysed or processed data. Moreover, the communication module is configured to establish a communication between the ring and the mobile communication device.

In an embodiment, the mobile communication device is connected to a communication network through a communication module. For example, the mobile communication device may be wirelessly connected to the ring by a wireless connection such as a WiFi, Bluetooth and the like.

The mobile communication device is associated with the user wearing the ring. In an embodiment, the mobile communication device includes a computing device which includes but not limited to a smartphone, a tablet computer, a phablet and a laptop.

In an embodiment, the mobile communication device is configured to collect the analysed raw data from the ring. Further, the mobile communication device is operable to perform deep data analysis of such raw data. It is to be understood that the mobile communication device includes required electronic elements, such as a processor, and algorithms to perform such deep data analysis.

In an example, the mobile communication device is operable to perform the deep data analysis of such raw data for example to determine a heart-rate-variability (HRV) from the inter-beat-interval. Also, a respiration rate (a signal related to breathing) can be determined from the PPG wave by analysing peak values thereof.

In another example, the deep data analysis includes determining a sleeping pattern of the user. Specifically, the data from the motion sensor may be processed by the mobile communication device to determine the sleeping pattern of the user. For example, based on the data from the motion sensor when the user went to bed and woke up can be identified. Also, based on the data from the motion sensor how long the user slept can be determined. Therefore, the data (i.e. when the user went to bed, when the user woke up and how long the user slept) enables in defining the sleeping pattern of the user.

In another example, the deep data analysis includes determining a sleep factor, such as a hypnogram for the rest period, for example when the user is sleeping. Specifically, the hypnogram is determined based on the measured motion data, photoplethysmogram waveform dynamics and heart rate dynamics using a classification algorithm, a decision tree, a neural network or equivalent. For a certain value of the hypnogram (e.g. with a resolution between 30 s and 10 min), a measurement period that is longer than the resolution of the hypnogram can be used (e.g. data from 10-20 minutes). This is because some characteristic features in the measured data appear more rarely than what is the aimed resolution of the hypnogram. Further, it gives an advantage to use more data from the history than from the future in certain features (e.g. deep sleep may start only after a certain duration of rest time but may stop when the rest time stops) in the determination of the hypnogram for a given time point. The hypnogram is used for analysing a sleep quality and various stages of sleep associated with a particular night. Similarly, the various other factors and parameters qualifying sleep may be used instead of a hypnogram. For example, the various sleep stages may include deep sleep, light sleep and rapid eye movement (REM) stage. Further, based on the absolute time at each stage and the percentage of various sleep stages the quality of sleep can be determined. Also, some or all of the following, i.e. how much the user typically accumulates on each stage, how much the user typically accumulates when weighted against the previous day's activity and what kind of feedback the user has given earlier in respect of nights that have properties similar enough to the night in question (the current night), may be also taken into consideration for determining the quality of the sleep.

In yet another example, the deep data analysis includes comparing sleep quality of the user for different nights. For example, the sleep quality may be compared by collecting various data of the user for those nights. Further, based on the comparison the sleep quality may be categorized into a good sleep, a bad sleep or an average sleep.

In an example, the categorization of the sleep quality may be determined with the amplitude of heart rates, duration of sleep and measured percentage of various sleep stages (i.e. deep sleep, light sleep and rapid eye movement stages). For example, the sleep quality may be said to be good if the heart rates is between 70-40 beats per minutes, the duration of sleep is about 7 hours and the percentage of the deep sleep is around 1 to 2 hours (10-20%) among the various sleep stages. Further, the user's feedback is taken to validate the sleep quality.

In an embodiment, the deep data analysis also includes measuring various physical provocations or non-provocations, as well as strength of such physical provocations or non-provocations. The physical provocations may be referred to as change in the physical activity level, i.e. when the user changes or attains a physical activity level from another physical activity level. For example, the physical provocations can be when the user stands up form a lying position, when the user starts walking form a sitting position, and the like. Further, the non-provocation may relate to situations when the user is subjected to no physical activity, i.e. when the user is sitting, lying down and the like.

In an embodiment, the various physical provocations or non-provocations may be measured by correlating the measured user's movement data and the heart rate. Specifically, the transitional changes in the activity of a person (i.e. standing up, sitting down, climbing stairs etc.) and the strength of provocation is measured. For example, the bodily reaction to provocation happens after a delay, therefore measurement of HR/HRV (where HR stands for heart rate) can be initiated only when such provocation is detected and the whole phenomena and bodily reactions during each phase (before, during and after transition/provocation) are measured.

In another example, the deep data analysis includes determining the user's stress level. Specifically, the user's stress level is determined by calculating the heart rate variability (HRV) for the activity period and the rest period, based on the measured heart rate. For example, the user's stress level may be determined based on the HR and/or the HRV, and/or the activity level and/or other sympato-vagal provocation, loading or a withdrawal of provocation. The HR, the HRV, and the activity level or provocation, the withdrawal of provocation, the load of a user are recorded at various times during the day and the values are correlated to arrive at a stress level of the user. The stress level is estimated based on a predetermined set of algorithms and analysis methods. Further, the physical disposition or sympato-vagal provocation and the activity levels of the user are automatically detected and the vital parameters, i.e., the HR and/or the HRV are recorded at different times.

For example, if there is no activity, i.e. no physical provocation but HR is high, the user may potentially be acutely suffering e.g. from a mental, psychological or emotional stress or is having a physiological stress reaction related to breathing (e.g. holding the breath) or other physiological stimulus like contraction, or a physiological stress reaction due to drinking or eating something that raises the pulse rate. Similarly, if there is any physical activity such as when the user is doing some physical exercise (walking, jogging or running), the bodily reactions are measured during the exercise period to detect the stress level.

In an embodiment, the mobile communication device is configured to calculate a readiness score for assessing readiness of the user. Specifically, based on long data, trends, cross-correlation analysis of the deep data analysis (i.e. heart rate variability, hypnogram, stress level and the like) the readiness score is calculated. Further, the long data, trends, cross-correlation analysis may be associated with a time period (for example a day, a week or a month) for which the deep data analysis is performed. Therefore, the measured user movements, and biosignals such as heart rate, sleep factor, heart rate variability and stress level for such time period are correlated to calculate the readiness score and thereby assessing readiness of the user.

The readiness score indicates a level of readiness of the user as well as the recovery of the user from the mental and physical load. The term 'readiness' used herein means also a return to a normal state of mental and physical strength (or energy level) after the mental and physical load. In an example, if the physical load is associated with an activity period (such as physical exercise), the readiness score may be based on the heart rate, heart rate variability and stress level of the user. For example, the readiness score may be good or high (such as about 90%), if the heart rate, heart rate variability and stress level of the user have returned to the normal state after the exercise. It is to be understood that the readiness score may be measured after a certain time period (for example half an hour) of the activity period. Similarly, if the mental load is associated with a rest period (such as sleep), the readiness score may be based on the movements, heart rate and sleep factor of the user. For example, the readiness score may be good or high (such as about 90%), if the user moves less, the heart rate is within a desired level (70-40 beats per minutes) and the sleep factor shows a good amount of deep sleep.

In one embodiment, historical data of the user is also used for calculating the readiness score. For example, the historical data may include information related to a medical history of the user, but also on historical data collected by the system itself. For example, the historical data may comprise data showing how the user typically recovers from a load. Otherwise, the historical data may include information related to past professional life, food habits, and the like. Therefore, it may be evident to those skilled in the art that the historical data may have substantial influence on measurement of the readiness score of the user.

In one embodiment, the method comprises providing the user with appropriate instructions, related to at least one of physical activity and mental activity, for improving the user's readiness score. That is, based on the readiness score, the user may be provided with appropriate instructions related to at least one of physical and mental load. Specifically, the appropriate instructions are provided to the user for improving the user's readiness score against such physical and mental load. For example, if the readiness score of the user is poor or low (such as about 40%) after doing exercise, the user may be instructed to take more rest such that the heart rate, heart rate variability and stress level return to normal state. This in turn may improve the readiness score related to the physical load. Similarly, if the readiness score of the user is poor or low (such as about 40%) after a sleep, the user may be instructed to sleep longer or to do mild exercise to have good quality sleep, which in turn may improve the readiness score related to the mental load.

In an embodiment, the mobile communication device is configured to visually present the readiness score to the user. For example, the mobile communication device is rendered with various user interfaces based on the readiness score. Specifically, the user interfaces are based on (or include) information related to the readiness score and the instructions for improving such readiness score. For example, the user interfaces may include a readiness score (shown with percentage i.e. 80-90%) and an instruction (such as 'sleep longer" or "do mild exercise'). Also, the user interface may include information related to the user's movement, heart rate, hypnogram, heart rate variability, body temperature, stress level and other data measured or obtained by the method and system. For example, the interface may show user's movement (i.e. number of miles the user has walked), heart rate (i.e. a digital representation of current beats per minute), duration of sleep, sleeping pattern, sleep factor such as hypnogram (various sleeping stages and their percentages) and the like.

According to another embodiment, the user interface is configured to also show separately the different elements which contribute to the readiness score. According to yet another embodiment the user interface also shows their effect on the readiness score (such as with signs + or −) and optionally also the history and/or estimate for following days. This embodiment allows the user to see in which direction the readiness score is evolving and at which rate it is changing. Moreover, the user interface may include a possibility for the user to enter data, such as an estimate of length of the following night's sleep and the interface would then be able to show a prediction of readiness score for the following day. Furthermore, the user may be given an estimate of time it takes to recover from one short night, for example.

Some possible elements to be shown according to this embodiment include (but are not limited to) activity of the previous day, heart rate at rest, sleep of the previous night, sleep debt (i.e. if the user did not sleep enough, the difference between the user's optimal amount of sleep and the amount of sleep the previous night or nights), activity of the day and body temperature.

The server is operable to calculate the readiness score and provide appropriate instructions to improve the user's readiness score. Specifically, the server of the system is operable to do the required analysis or processing of data (i.e. the deep data analysis and long data, trends, cross-correlation analysis of the deep data analysis) for rendering the user interface on the mobile communication device. For example, the deep data analysis may be partly performed in the server and partly performed in the mobile communication device; otherwise the deep data analysis may be completely performed in the server. Similarly, the long data, trends, cross-correlation analysis of the deep data analysis may be partly or completely performed by the server. Further, the server may be configured to collect the raw data from the ring directly or may be configured to collect the raw data indirectly through the mobile communication device. Therefore, the server may perform the required analysis for rending the user interface related to the readiness score and the instruction (i.e. various aspects subjected to assessing readiness and recovery of the user from mental and physical load). It is to be understood that the server includes required electronic elements, such as a processor, and algorithms to perform such analysis.

In an embodiment, the server is communicatively coupled to the user terminal through a communication network which can be wired, wireless or a combination thereof. For example, the communication network includes, but are not limited to, Local Area Networks (LANs), Wide Area Networks (WANs), Metropolitan Area Networks (MANs), Wireless LANs (WLANs), Wireless WANs (WWANs), Wireless MANs (WMANs), the Internet, second generation (2G) telecommunication networks, third generation (3G) telecommunication networks, fourth generation (4G) telecommunication networks, and Worldwide Interoperability for Microwave Access (WiMAX) networks.

Some examples of concrete parameters that may be defined and monitored in respect to daily readiness to perform, as well as their effect on readiness, are listed below.
Previous or last night; the quantity and quality of sleep; getting enough sleep improves daily readiness.
Sleep balance (sleep debt); the sum of how much accumulated sleep over past 1-3 weeks differs from individual sleep needs; insufficient sleep results in sleep debt that reduces daily readiness.
Previous day (physical activity); excess sedentary time, excess vigorous intensity and excess total volume of physical activity reduces daily readiness, but also lack of sedentary time, exercise and physical activity reduce daily readiness.
Activity balance (cumulative level compared to user's own history); the activity balance is calculated over a period of for example 1-3 weeks and compared to the user's long term activity (e.g. 1-12 months average or typical level changes, best readiness is achieved during easy periods when activity levels are somewhat below average (i.e. not excess of activity, but not zero activity levels either).
Body temperature; changes in maximal nightly skin temperature can be markers of sickness and clear deviation from user's norm reduces readiness; body temperature may also be an indication of the menstrual cycle for pre-menopausal women.
Resting heart rate; changes in minimum nightly heart rate are markers of stress that usually reduces readiness; a user's resting heart rate may change for various reasons and thus maximum readiness is typically encountered when resting heart rate is somewhat below user's norm (but not too much below as that could be associated with excess fatigue).
Resting heart rate-based recovery index; how long restorative sleep the user reached after his/her hear rate had stabilized to the proximity of the resting heart rate; longer accumulated bedtime/sleep/deep sleep/deep+REM after heart rate has stabilized predicts improved readiness; this contributor will react also to alcohol consumption and late exercise, among other things, both challenging the user's readiness.

The various data or parameters may be weighted, based on how each contributes to the readiness score. Some principles used in the weighting may be for example as follows. Some of the parameters have monotonously decreasing contribution, while some others have monotonously increasing contribution. Some of the parameters have an optimal area and the readiness decreases in both directions (i.e. below and above the optimal area). Furthermore, the device and method may be configured to take the body temperature in account when weighting the data, i.e. the weighing may be performed continuously. For example, if the user's temperature is within a pre-defined, normal scale, its weight can be minimal and a "normal" weighting is used for the other parameters or data. However, if the user's temperature is elevated (i.e. above a pre-determined limit), its weight can be big and optimal activity levels can be lowered accordingly. Again, the device may be set such that it is able to define the normal scale of temperature for the user.

Still further, the method and device may be configured to take into account the calendar. For example, the device may be able to recognise the time of the year (such as winter, spring, summer or autumn) or weekdays from weekends. This information may be taken into account in the need of sleep, for example, as typically persons sleep more in the winter than in the summer. This information may also be taken into account in the history data. For example, the device may recognise that the current month is January, and also compare current data to data from a previous year's January.

According to a preferred embodiment, the output in the device (i.e. on its user interface) is a percentage as a readiness score. It may also show the main contributors for example as a graphical element (for example showing a bar for each contributor). One example of a simple interpretation of single readiness contributors is the following.

<35% means that the user needs to take actions with this contributor in order to improve the readiness;

35-70% means that the user could pay attention to this contributor in order to improve the readiness;

70-85% means that this particular contributor is below recommended levels—apparently helping the user to manage his/her daily requirements; and 85-100% means that this particular contributor is within general recommendations and also good at the user's individual level, i.e. to the level that it boosts the user's readiness to perform the given day.

The user interface may also comprise a means for warning if one or more contributors are above a pre-defined maximum level. It is evident that the combination of challenging and boosting contributors can be displayed and mathematically presented in many different ways. However, the presented example calculations give one example on the solution to the problem how one could combine the complex and occasionally contradictory contributions of sleep, activity and body responses to the readiness of the user (body responses for example due to sickness or environmental factors). It may be useful to show the combination of factors for several reasons. For example, not everybody can similarly adjust every parameter (shift work, other responsibilities or preferences or life habits or temperament) so it is necessary to leave the freedom and possible choice to the user. Moreover, each factor may be important on different times (holiday, weekday/weekend day, depending on family situations or training phase etc.).

The readiness score can be scaled on many different ways. One example is a scale between 0 and 100, where 85 means sufficient or normal or adequate readiness for the current day. This value is intended to correspond with the user's average condition, provided the user has been living his/her normal life. In addition, the device and method may comprise certain means to recognize abnormal life, as is explained below.

One example of possible calculations and effects of the different variables and parameters in the present method and device is given below.

1. Sleep1_previous_night_quality
a. Device calculates a sleep score for each night (0-100). Alternative could be e.g. total sleep time/9 hours (the latter is the maximum sleep need that can be expected for a normal individual), or deep+REM/4.5 hours.
b. Device calculates user specific average and deviation from earlier sleep scores from the same user
   Alternative can be human specific norm that is especially practical in the beginning when individual data is not available. A human specific norm can also be used at later stages as a comparison to the user specific average.
c. Device calculates how much and in which direction current Sleep1_previous_night_quality differs from what is an adequate level for user (named as Average) $Z\_index=(Current\ value-Average)/Deviation$
   Z_index is 1 when your value is 1 deviation higher than your average.
d. Device controls that user's average is good enough to be regarded as a reference for "sufficient" or "adequate" sleep score—if not, the device selects a predetermined minimum/maximum sleep score (for example 85/95) that can be regarded as sufficient or adequate for reference and uses that value instead of user's own Average value.
e. Device also controls that user's deviation is within sensible range (e.g. 5-10)—otherwise the measurement can become too sensitive or insensitive to changes.
f. Device estimates the contribution of previous night's sleep to the Readiness to perform the following day so that it gives a higher contribution the better the sleep score was the previous night
   $ReadinessContributors(1)=85+12.5*Z\_index\_1;$
   In practical terms, maximal contribution to the daily readiness, by Sleep1_previous_night_quality, is achieved for example when sleep score is both minimum 90% and higher than user's long term average sleep score by a margin that depends on sleep score variability.

2. Sleep2_Balance
g. The user is supposed to be have higher readiness the more he/she has slept during preceding 2 weeks.
h. Device registers total sleep time on several nights $S(0)=7.5\ h,\ S(1)=8.0\ h,\ S(2)=7.8\ h,\ S(3)=6.0\ h,\ S(4)=5.8\ h,\ S(5)=7.2\ h,\ \ldots$
i. Device estimates what is user's individual sleep need
   Device calculates user's long term average, and controls that it is between normative range (7-9 hours, in a preferred embodiment the acceptable range can also be age dependent).
j. Device calculates how much sleep time differs from individual estimated sleep need
   $D(0)=7.5\ h-Avg,\ D(1)=8.0\ h-Avg,\ D(2)=7.8\ h-Avg,\ D(3)=6.0\ h-Avg$, and so on.
k. Device also calculates how much user's sleep durations typically vary between nights (SleepDeviation), and checks that the deviation is not too small or too high to represent user's sensitivity to changes (acceptable deviation range can be e.g. 25-45 minutes).
l. Device calculates a weighted mean of the differences (weighing is needed for smoothing the effect on the edge of the window)
   $SleepBalance=W(0)*D(0)+W(1)*D(1)+W(2)*D(2)+$ and so on (exponentially decreasing weight as time elapses).
m. The user is supposed to have the higher readiness the more he/she has slept during preceding 2 weeks
   $ReadinessContributors(2)=85+30*(SleepBalance/SleepDeviation));$
   In practical terms, maximal contribution to the daily readiness, by Sleep2_Balance, is achieved for example when average two week sleep time is both 7-9 hours and exceeds long term average sleep time by 15-20 minutes, depending on that average.

3. Activity1_Last_day
n. Z-index is calculated for total daily movement Z_index_3a (from distance, steps, kcal and/or equivalent kilometers etc.) in a similar way as presented above for the sleep score when estimating the contribution of Sleep1_previous_night_quality (i.e. utilizing user specific average and deviation, and controlling if user specific average is a good value to be the proxy for a normative reference point (acceptable limits e.g. 4-20 km/day). Correspondingly, Z-index is calculated separately for vigorous intensity activity Z_index_3b (from time or METmins or kcals accumulated at high intensity exercise) and sedentary behaviour Z_index_3c (e.g. accumulated daily sedentary time or number of inactive periods that last longer than a pre-determined threshold period of e.g. 30 minutes, or their combination).

o. The user's readiness is the lower the higher his/her total daily movement has been (in kcal, distance, steps, eq. km, etc.), the more vigorous and more sedentary activity he/she had during the previous day. In a preferred embodiment more value is given to vigorous/intensive physical activity. In our example vigorous intensity accumulates also total activity, this arrangement leads to pronounced effect of vigorous intensity. More sedentary day also decreases the readiness.
ReadinessContributors(3)=85−6*($Z\_index\_3a$+$Z\_index\_3b$+$Z\_index\_3c$; In practical terms maximal contribution to the daily readiness, with regards to the physical activity of the last day, is achieved after a day which has about one third less of total activity, vigorous activity, AND sedentary time compared to long term averages. The contribution is weaker both with very little activity, or excess of activity.

4. Activity2_balance p. A weighted 2-week measure of user's daily activity is calculated in an analogue way to sleep balance above including the checks. Total activity can be expressed in eq. km, kcal or kcal/body weight, steps and so on.

q. ReadinessContributors(4)=100−60*abs(0.25+(ActivityBalance/ActivityDeviation)); In practical terms maximal contribution to the daily readiness, with regards to the physical activity of the last day, is achieved when average two week total activity is 10-60% less than long term average total activity (the margin depends on user's long term average and daily variability in long term activity). Increasing distance from that level in either way decreases the contribution to the readiness.

5. Body_Response1_Temperature r. The wearable device, such as the ring, can be programmed to record user's maximal stable temperature during the night, or during certain time of the night when ring measured distal body temperature best matches with the body temperature. It may be favorable to make the measurement when core body temperature is the lowest in circadian variation i.e. typically between 2 and 5 a.m.

s. In an analogue way to parameters1 (last night's sleep) and parameter 3 (previous day's activity), $Z\_index\_5$ is calculated for nightly temperature reading. The user has the lower readiness the more his/her night_time temperature deviates from his/her long term mean, taking his/her normal variation into account.

t. It is more certain that an elevated temperature is causing decreased readiness compared to a lowered temperature, as the latter can sometimes be a measurement error: if $Z\_index\_5$>0.15, ReadinessContributors(5)=105−25*$Z\_index\_5$; elseif $Z\_index\_5$<−0.50, ReadinessContributors(5)=105+10*$Z\_index\_5$; else ReadinessContributors_5=100; end.

u. In favorable solution women's period/menstrual cycle is taken into account so that the biphasic temperature (rise in the middle of the period and fall in the end) is taken into account so that sensitivity to a sickness, for example, is not lost.
In practical terms the highest contribution to readiness by body temperature reading is achieved when the filtered body temperature that was determined during the night differs from long term average by less than 0.4 C, the exact number also depending on the normal variability of the user's temperature.

6. Body_Response2_Resting HR v. User's readiness is the lower the more his/her resting HR deviates from his/her norm—in a favorable solution there is some asymmetry, as it seems to be a sign of good recovery and a positive physical training effect to have resting heart rate little below norm.

w. In an analogue way to parameters1 (last night's sleep) and parameter 3 (previous day's activity) and parameter5 (body temperature), $Z\_index\_6$ is calculated for nightly resting HR reading.

x. if $Z\_index\_6$>−1, ReadinessContributors(6)=87.5−30*$Z\_index\_6$; else ReadinessContributors(6)=116+16*$Z\_index\_6$;
In practical terms, the highest contribution to readiness regarding this parameter is reached when resting heart rate is 2-5 bpm below long term average (margin depends on variability and average value of the long term HR). Strongly negative values indicate only slightly decreased readiness, while elevated HR is a clear indicator of negative contribution.

7. Body_Response3, Bedtime or sleep accumulated after HR has stabilized y. One body response parameter within the readiness score is the amount of rest after reaching resting zone of heart rate. This is influenced by for example alcohol consumption, heavy eating or a too intense sport late in the evening.

z. The user has the higher readiness the more bedtime he/she has accumulated after he/she has got within 1-3 bpm to his/her HR minimum.

æ. $Z\_index\_7$ is calculated in an analogue way to Z_indexes explained above. The acceptable range for normative user reference can be for example 4-7 hours.

ø. ReadinessContributors(7)=85+15*$Z\_index\_7$;
In practical terms the highest contribution to readiness regarding this parameter is reached if user has accumulated 5-7 hours of bedtime, preferably sleep, after the lowest heart rate period of the night has been reached (margin depending on long term average and deviation of that time)

All ReadinessContributors have been scaled between 0 . . . 100. Finally it is useful to check that the scale is maintained as some of the equations presented above may result in numbers that fall outside this scale.

for i=1:size(ReadinessContributors), if ReadinessContributors(i)<0, ReadinessContributors(i)=0; elseif ReadinessContributors(i)>100, ReadinessContributors(i)=100; end The present disclosure further relates to a user interface comprising an area indicating a readiness score of the user, an area indicating parameters affecting the readiness score and an area indicating change of at least one of said parameters with respect to an earlier point of time. Some examples of suitable user interfaces are given below in connection with the drawings. The user interface may for example include indications on readiness score on a three-level scale, such as bad, average, good. Different components of the readiness score may also be shown, as well as their influence on the readiness score. The user interface may also include a possibility for the user to simulate different ways of improving the readiness score, for example when the ideal way to improve readiness score would be to do a physical exercise for an hour, but the user only has a half an hour available. The user could then for example choose between different sports available to him/her (such as gym, running or swimming), and choose the one having the most positive effect on the readiness score. Users that are for example travelling and busy with business meetings etc, could thus optimise their use of free time. The user interface may also show past readiness scores as well as what has influenced them.

There are a number of advantages for using a ring device instead of a wrist device. For example, many persons prefer to wear a bracelet or wristlet on his/her wrist rather than a measuring device. Furthermore, a ring is optimal for measuring HR/HRV optically, as in a finger, two arteries are close to the skin. These arteries are on the palm side of the hand and covered by soft tissue, the wearable ring does thus not need to be tightened to ensure a good contact to the skin. Thus the position of the ring in relation to the finger and arteries typically stays very stable although the palm is turned up and down and in consequence, the ring does not move in relation to the arteries. Furthermore, in a wrist there are two bones and turning the palm up and down means that the bones are twisted which then causes the wrist device to move with respect to the skin underneath the device and thus also with respect to the arteries in the wrist. A yet further advantage is that if the user wants to change the measurement position due to inconvenience in one finger (for example abrasion, rubbing, scar), he/she can change the ring easily from one finger to another, whereas the choice of measurement position is more limited for wrist-worn devices. In case of swelling, the ring can also be changed to a smaller finger. A ring is also a much lighter device to carry than a wrist device.

The present disclosure provides a method and a system for assessing readiness of a user. Specifically, the method and the system are configured to calculate the readiness score and provide appropriate instructions to improve the readiness score against such mental and physical load the user is subjected to. Further, the readiness score is based on real time, exhaustive and comprehensive analysis of data (i.e. the user's movement, biological signals and the like) which makes the method and the system of the present disclosure to provide appropriate instructions to the user. Therefore, the appropriate instructions enable the user to manage his or her health related aspects (for example sleep, stress level and physical activity).

DETAILED DESCRIPTION OF THE DRAWINGS

Referring now to the drawings, particularly by their reference numbers, FIG. 1 is a schematic illustration of a system 100 for assessing readiness of a user, in accordance with an embodiment of the present disclosure. The system 100 includes a ring 102, a mobile communication device 104 and a server 106. The ring 102 is communicably coupled to the mobile communication device 104 by a communication network 120 and the mobile communication device 104 is communicably coupled to the server 106 by communication network 122.

The ring 102 is associated with a user (not shown) and configured to measure user's movements and a heart rate associated with the user. Specifically, the ring 102 includes optical electronics 130 (such as at least one photon source and at least one photon detector) and at least one motion sensor 132 (such as an accelerometer, a gyroscope, a magnetic field sensor or a combination thereof). The ring also includes other electronic 134 configured to collect and analyse raw data (i.e. data of the motion sensor and the optical electronics). The other electronic components 134 include but is not limited to a controller, a microprocessor, a memory and a communication module.

The mobile communication device 104 and the server 106 are configured to collect the raw data generated by the ring 102. Further, the server 106 are configured to perform a deep data analysis of the raw data in order to find heart rate variability, hypnogram, stress level and the like. It is also possible that part or all of the analysis is performed by the mobile communication device, in which case the server is incorporated in the mobile communication device. Also, the mobile communication device 104 and the server 106 are configured to perform long data, trends and cross-correlation analysis of the deep data analysis in order to calculate a readiness score (i.e. based on the user's movements, heart rate, heart rate variability, hypnogram and stress level). Moreover, based on the readiness score the user is provided with appropriate instructions to improve the readiness score against the mental and physical load the user is subjected to. Specifically, the mobile communication device 104 is configured to visually present the readiness score to the user with the help of various user interfaces (or a single interface incorporating all the information). The user interfaces are based on (or include) information related to the readiness score, the instructions and data associated with user's movement, heart rate, hypnogram, heart rate variability and stress level. The raw data analysis may also be used to determine another sleep factor than hypnogram, as explained above.

Figure 2:
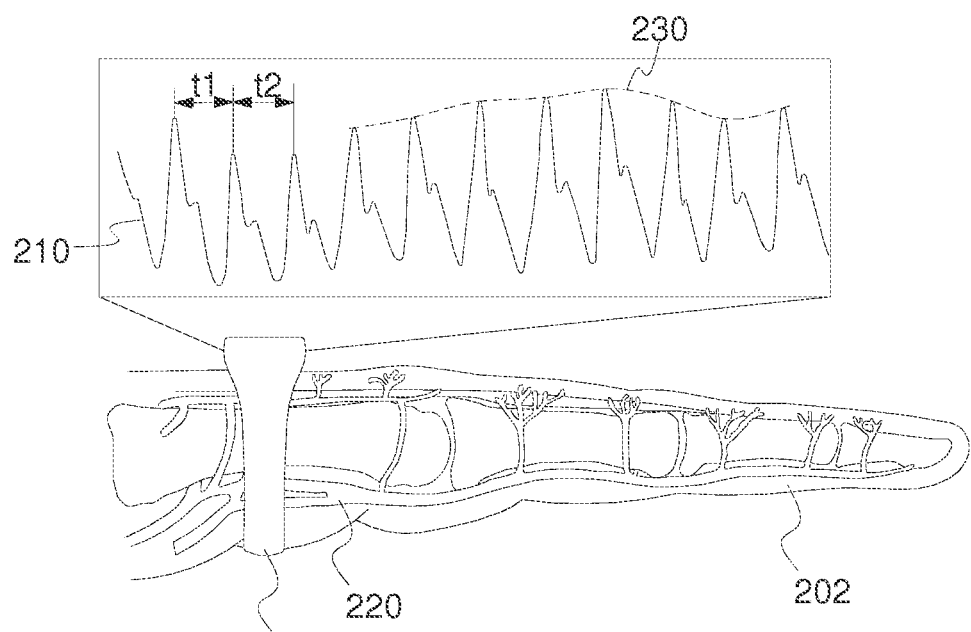
FIG. 2 is schematic illustration of a ring worn at a finger of the user for collecting a heart rate of the user, in accordance with an embodiment of the present disclosure.

Referring now to FIG. 2, shown is a schematic illustration of a ring 200 worn on a finger 202 for collecting a heart rate of the user, in accordance with an embodiment of the present disclosure. Specifically, the ring 200 is configured to collect the heart rate of the user (during both an activity period and a rest period) using the optical electronics 130 (shown in FIG. 1). As shown, a measured graph includes a heart rate pulse wave form 210 as function of time. The measurement is done by measuring a change of blood volume using PPG of blood vessels 220. Further, from the wave form 210 an inter beat interval (IBI) is determined. The IBI is the time between two beats such as time t1 and t2, and is also referred to as the heart rate.

Moreover, from the wave form 210 a heart rate variability (HRV) can be determined by subtracting inter beat intervals, for example t1–t2. Also, a respiration rate can be determined from the wave form 210 by analyzing peak values. As shown, a respiration curve 230 is based on the peak values, which correspond to a rate of breathing of the user. The respiration curve 230 is used to analyze exercise impact and recovery of the user together with other heart rate related indications (IBI, heart rate, heart rate variability). It to be understood that the heart rate variability and the rate of breathing may be calculated by the mobile communication device 104 and/or the server 106 (shown in FIG. 1), as a part of the deep data analysis. The ring 200 is also configured to measure user's movement, which is explained in conjunction with FIG. 3.

Figure 3:
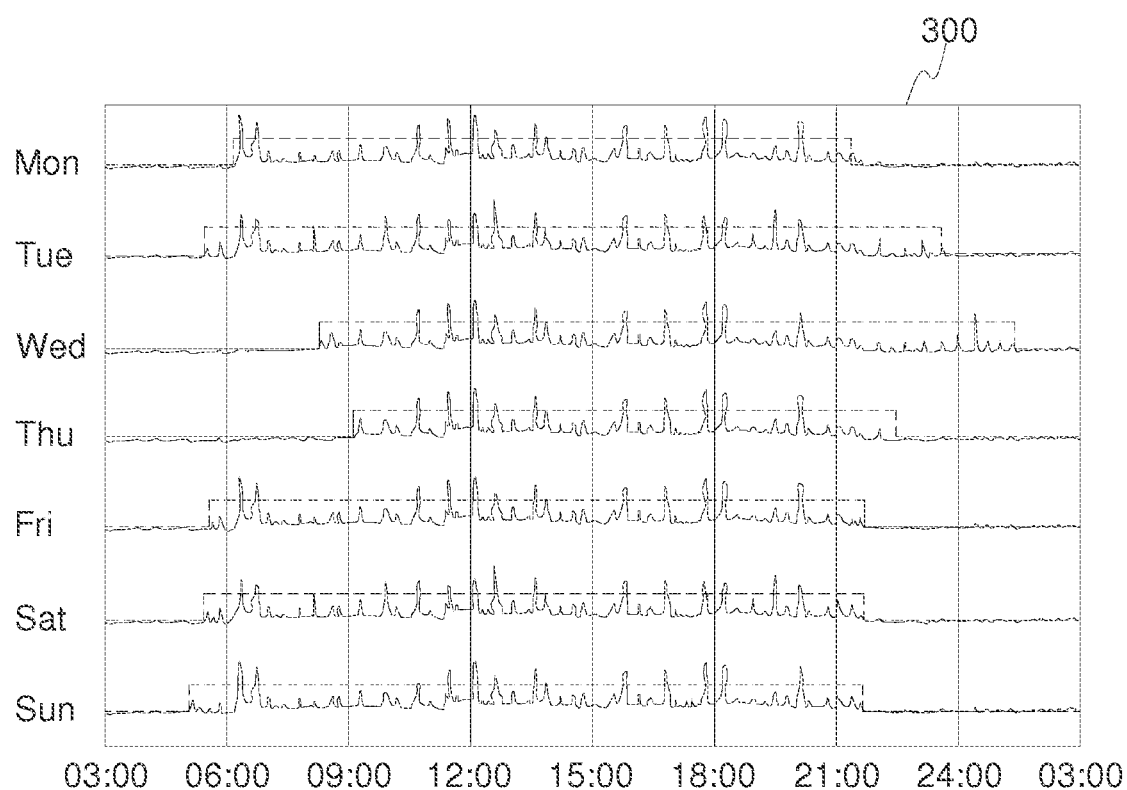
FIG. 3 is a schematic illustration of a graph showing physical activity data of the user for a week, in accordance with an embodiment of the present disclosure.

Referring now to FIG. 3, shown is a schematic illustration of a graph 300 related to physical activity data of the user for a week, in accordance with an embodiment of the present disclosure. Specifically, the graph 300 shows data collected from the motion sensor 132 (shown in FIG. 1) for a week (i.e. Mon-Sun) for both the activity period and the rest period. As shown, the data shows more movement on the time when the user is awake (i.e. during the activity period) than when the user is sleeping (i.e. during the rest period). Based on such data a sleeping pattern (when the user went to bed and when woke up) can be determined. Also, a total number of hours the user slept on a particular night can be determined. For example, as shown, on Mon the user slept form about 9 pm to 6 am (i.e total of 9 hours sleep), whereas on Tus the user slept form about 12 am to 6 am (i.e total of 6 hours sleep).

Figure 4:
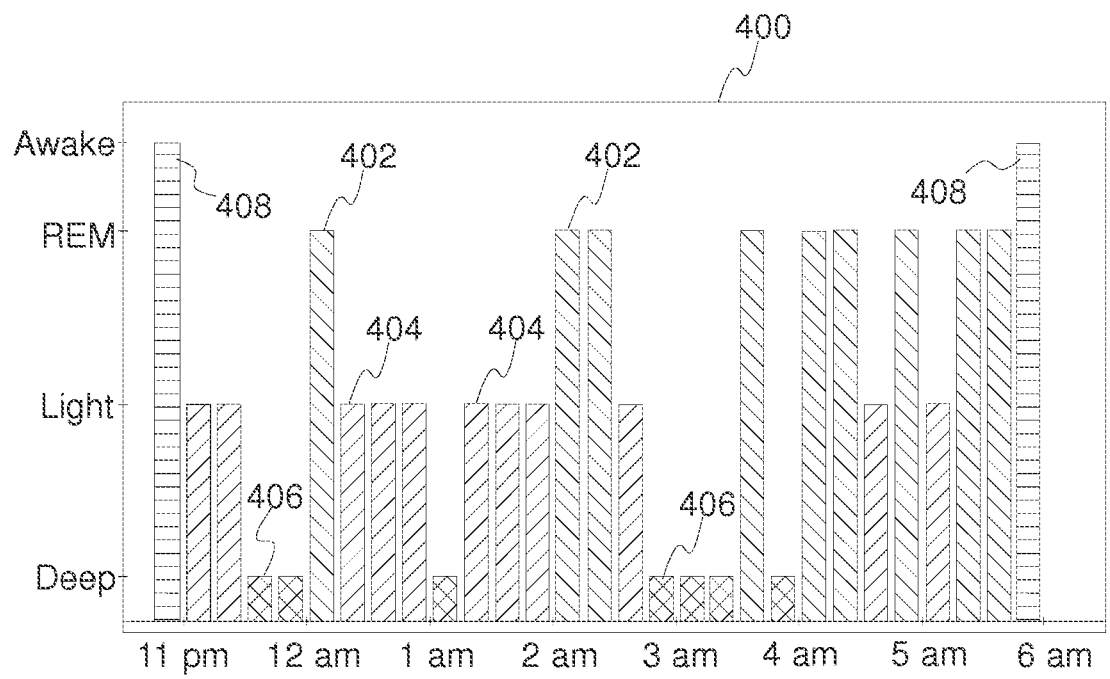
FIG. 4 is a schematic illustration of a hypnogram of the user, in accordance with an embodiment of the present disclosure.

Referring now to FIG. 4, shown is a schematic illustration of a hypnogram 400 of the user, in accordance with an embodiment of the present disclosure. The hypnogram 400 depicts a quality of sleep the user had on a particular night. Specifically, the hypnogram 400 is determined using a heart rate wave form of the user for that particular night. The hypnogram 400 is used to analyze sleep quality and stages (i.e. deep, light, REM (Rapid eye movement)). As shown, the hypnogram 400 includes various stages of sleep i.e. REM 402, light sleep 404 and deep sleep 406. Also, the hypnogram 400 includes indications 408 when the user is awake (i.e. before attaining sleep and after getting up from the sleep).

Figure 5:
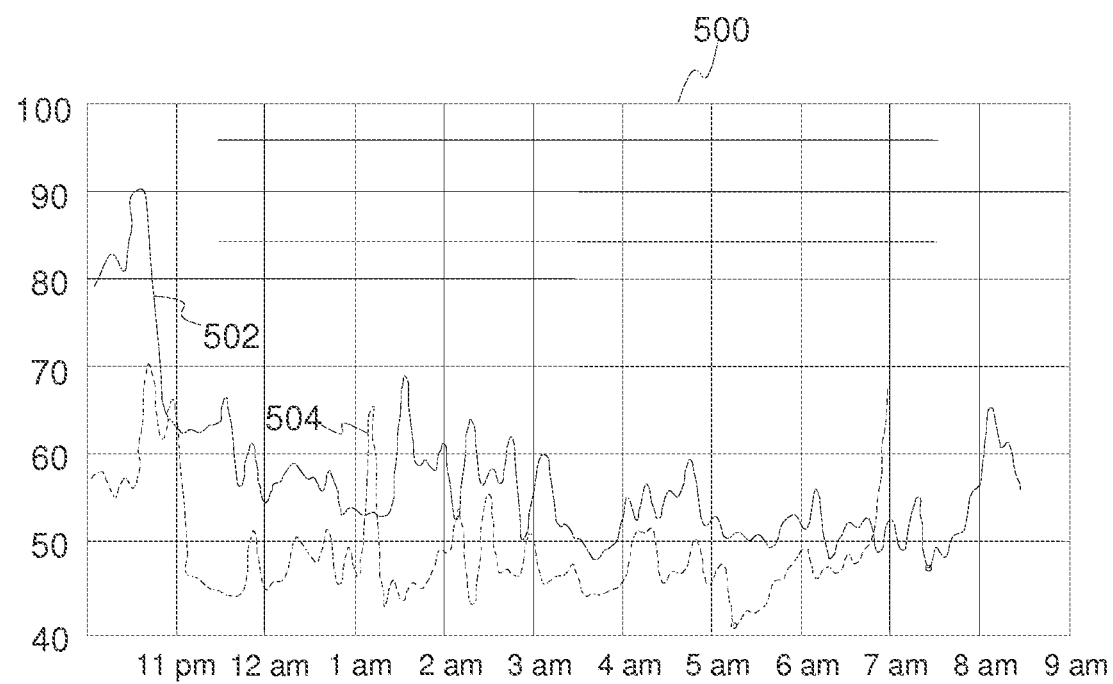
FIG. 5 is a schematic illustration of a graph showing collected heart rate of the user for two nights, in accordance with an embodiment of the present disclosure.

Referring now to FIG. 5, shown is a schematic illustration of a graph 500 related to collected heart rate of the user for two nights, in accordance with an embodiment of the present disclosure. The graph 500 shows the collected heart rate of the user for two different nights, for example last two nights. As shown, a heart rate wave form 502 depicts an example of a 'good night sleep' associated with one particular night. The determination of the good night sleep is based on the wave form 502 (which may be associated with a 'normal day' of the user) having a measurement i.e. lowest HR 41 bpm (beats per minute) at about 5:15 (6 hours 15 min of sleep). Also, determination of good sleep is substantiated with the user's feedback.

The graph 500 also shows a heart rate wave form 504 depicting an example of a 'bad night sleep' associated with another night. The determination of the bad night sleep is based on the wave form 504 (which may be associated with a day when the user did too much exercise just before sleeping). For example, the wave form 504 includes a measurement i.e. lowest HR is 47 bpm at 7:30 AM which is 8 hours 15 min after bedtime, showing dramatic change between the two days. Therefore, the wave form 504 shows that the heart rate decreases slowly down to normal resting pulse and thus disturbs the sleep. Based on such measurements the user may be instructed to ease up for example 2 hours before predicted sleeping time to make sure that the heart rate is not too high during the sleep period.

Figure 6:
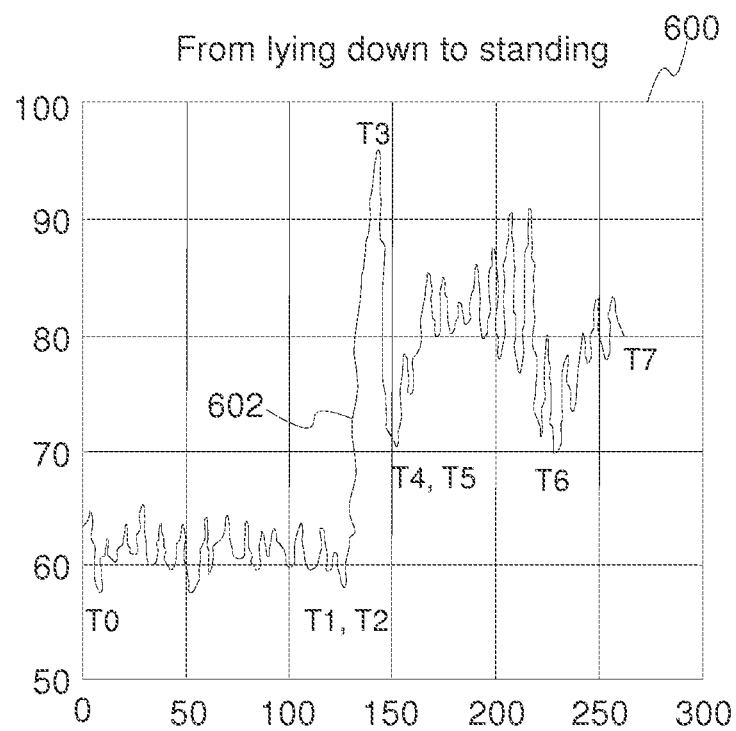
FIG. 6 is a schematic illustration of a graph showing provocation measurement of the user, in accordance with an embodiment of the present disclosure.

Referring now to FIG. 6, shown is a schematic illustration of a provocation measurement of the user, in accordance with an embodiment of the present disclosure. Specifically, the FIG. 6 illustrates a graph 600 with a heart rate wave form 602 associated with a provocation measurement (i.e. when the user stands from a lying position). For example, while the user lies in bed in the morning after a night of sleep, the heart rate measurement begins at time T0. Thereafter, when the user stands up, the heart rate measurement begins at time T1. The user stands still and pulse data is measured for subsequent times T2-T7. Further, the strength of physiological provocation/activity is measured during each phase with an accelerometer.

Figures 7, 8:
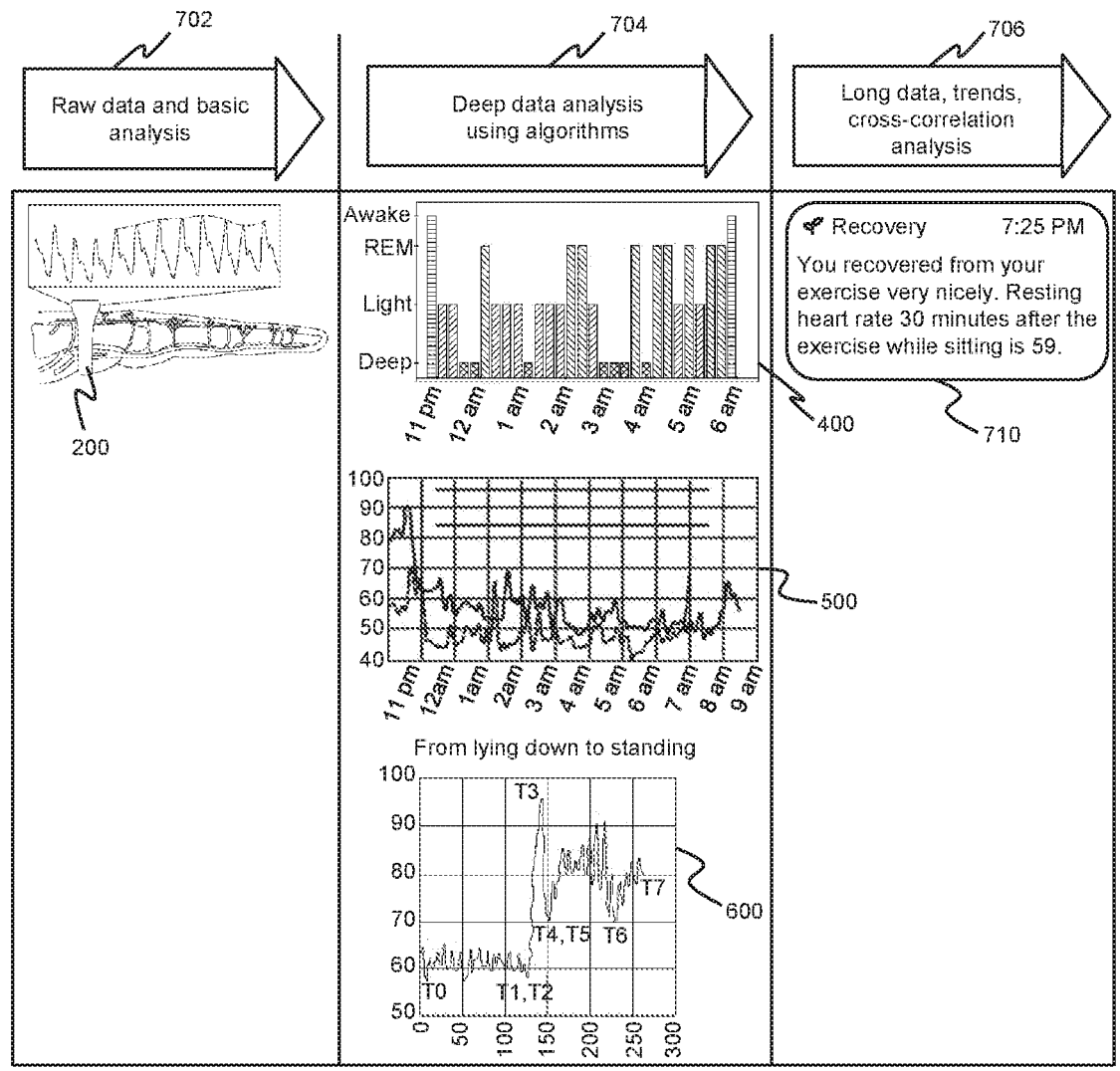
FIG. 7 is a schematic illustration of various stages involved in calculating a readiness score by the system of FIG. 1, in accordance with an embodiment of the present disclosure.
FIG. 8 is an illustration of steps of a method for calculating a readiness score by the system of FIG. 1, in accordance with an embodiment of the present disclosure.

Referring now to FIG. 7, shown is a schematic illustration of various stages involved in calculating a readiness score by the system 100, in accordance with an embodiment of the present disclosure. As shown in FIG. 7, the calculation of the readiness score includes the following stages, for example, a first stage 702 which relates to measuring raw data and basic analysis of the raw data. Further, a second stage 704 is related to the deep data analysis, i.e. when the mobile communication device 104 and the server 106 (shown in FIG. 1) are configured to perform the deep data analysis of the raw data in order find various health related aspects of the user. As shown, the second stage 704 includes determining the hypnogram 400, the determining of heart rate variability to compare sleep quality (shown with the graph 500) and the provocation measurement (shown with the graph 600).

It may be evident to those skilled in the that the second stage 704 also includes various other kinds of measurements such as the respiration rate, the stress level measurement and the like. Moreover, FIG. 7 also illustrates a third stage 706 which includes long data, trends and cross-correlation analysis of the deep data analysis (i.e. heart rate variability, sleep factor, stress level and the like measurement performed in the second stage 704). Based on the measurement associated with the third stage 706, a readiness score is calculated, which is an indication of a level of readiness of the user. Further, appropriate instructions are provided to the user for improving the user's readiness score. As shown, an appropriate instruction 710 includes "You recovered from your exercise very nicely. Resting heart rate 30 minutes after the exercise while sitting is 59".

Referring now to FIG. 8, shown are steps of a method 800 for calculating a readiness score by the system 100, in accordance with an embodiment of the present disclosure. Specifically, the method 800 depicts the various stages involved in the measurement of the readiness score, as explained in conjunction with FIG. 7.

At stage 802, raw data is collected and analysed by a wearable device (such as the ring 200). The raw data is associated with the user's movements and the heart rate.

At stage 802, deep data analysis is performed on the raw data using algorithms in a user communication device or a server. Specifically, the deep data analysis is performed in at least one of the user communication device and/or the server. The deep data analysis provides various health related aspects associated with the user such as the heart rate variability, respiration rate, sleep factor, stress level, provocation measurement and the like.

At stage 806, instructions are provided to the user based on long data, trends and/or cross-correlation analysis of the deep data analysis. Specifically, a readiness score is calculated from the various data, such as the heart rate variability, respiration rate, sleep factor, stress level, provocation measurement and the like. Thereafter, appropriate instructions are provided to the user for improving the user's readiness score against the mental and physical load.

Referring now to FIGS. 9-12, shown are schematic illustrations of user interfaces rendered on a mobile communication device, in accordance with various embodiments of the present disclosure.

Figure 9:
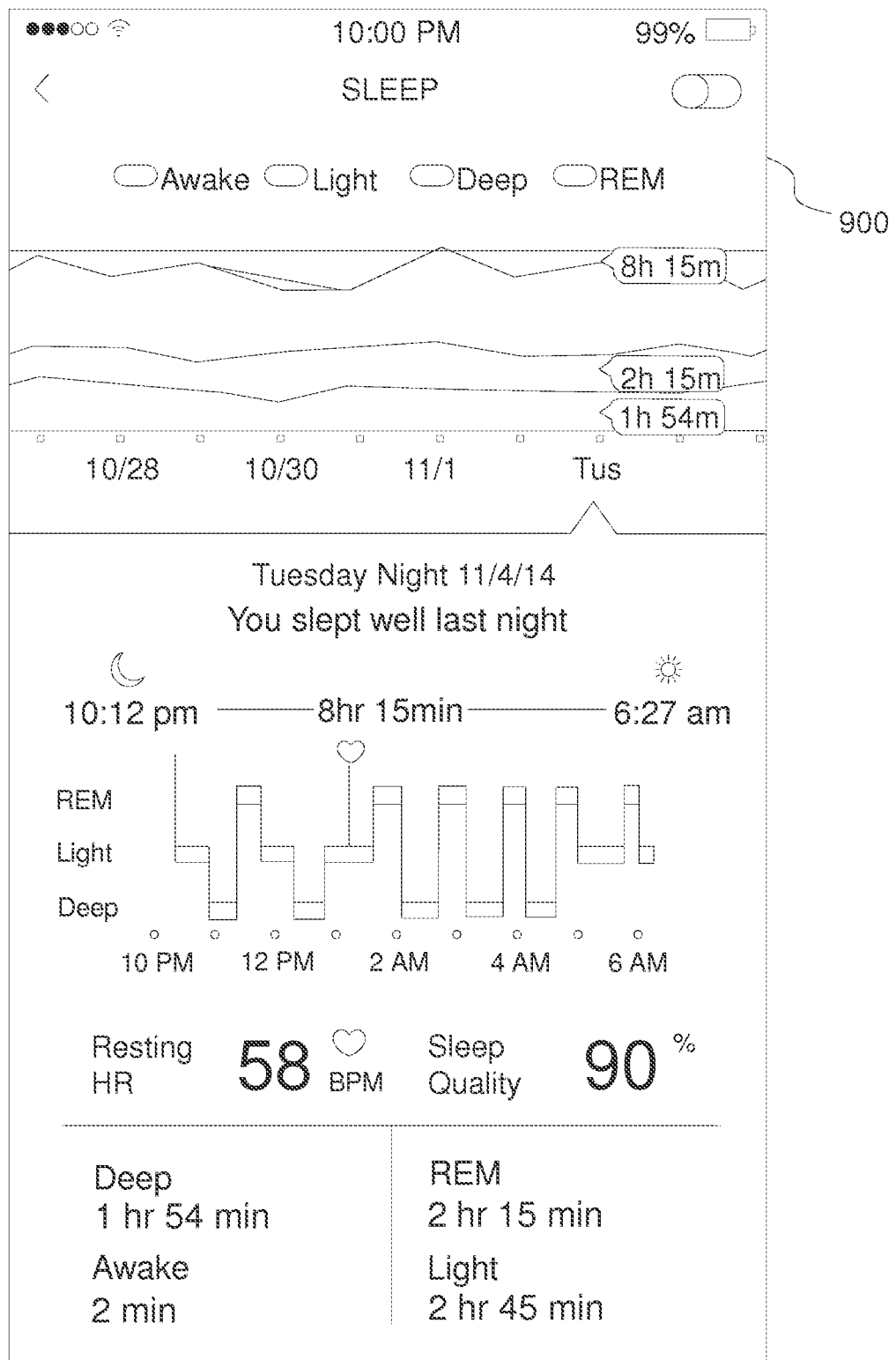
FIGS. 9-12 are schematic illustration of user interfaces rendered at a mobile communication device, in accordance with various embodiments of the present disclosure.

FIG. 9 shows a user interface (UI) 900 rendered on the mobile communication device (such as the mobile communication device 104 of FIG. 1). As shown, the UI 900 provides statistical information related to a particular night's sleep (for example last night's sleep). For example, the UI 900 provides information about the various stages of sleep (i.e. the REM, the light sleep and the deep sleep) for a particular night. Further, the UI 900 provides information related to weekday and date, such as 'Tuesday Night-Nov. 4, 2014'. Also, the UI 900 provides information how well the user slept (for example 'You slept well last night'). Moreover, the UI 900 provides information when the user went to sleep, when the user woke up and how long the user slept (for example the user went to sleep at 10:12 pm, woke up at 6:27 am and slept for 8 hr 15 min). Also, the UI 900 provides information about Resting HR and sleep quality (for example 58 bpm and 90% respectively). Furthermore, the UI 900 provides information related to measurement of the various stages of sleep (for example, deep sleep 1 hr 54 min, REM 2 hr 15 min, awake 2 min and light sleep 2 hr 45 min).

Figure 10:
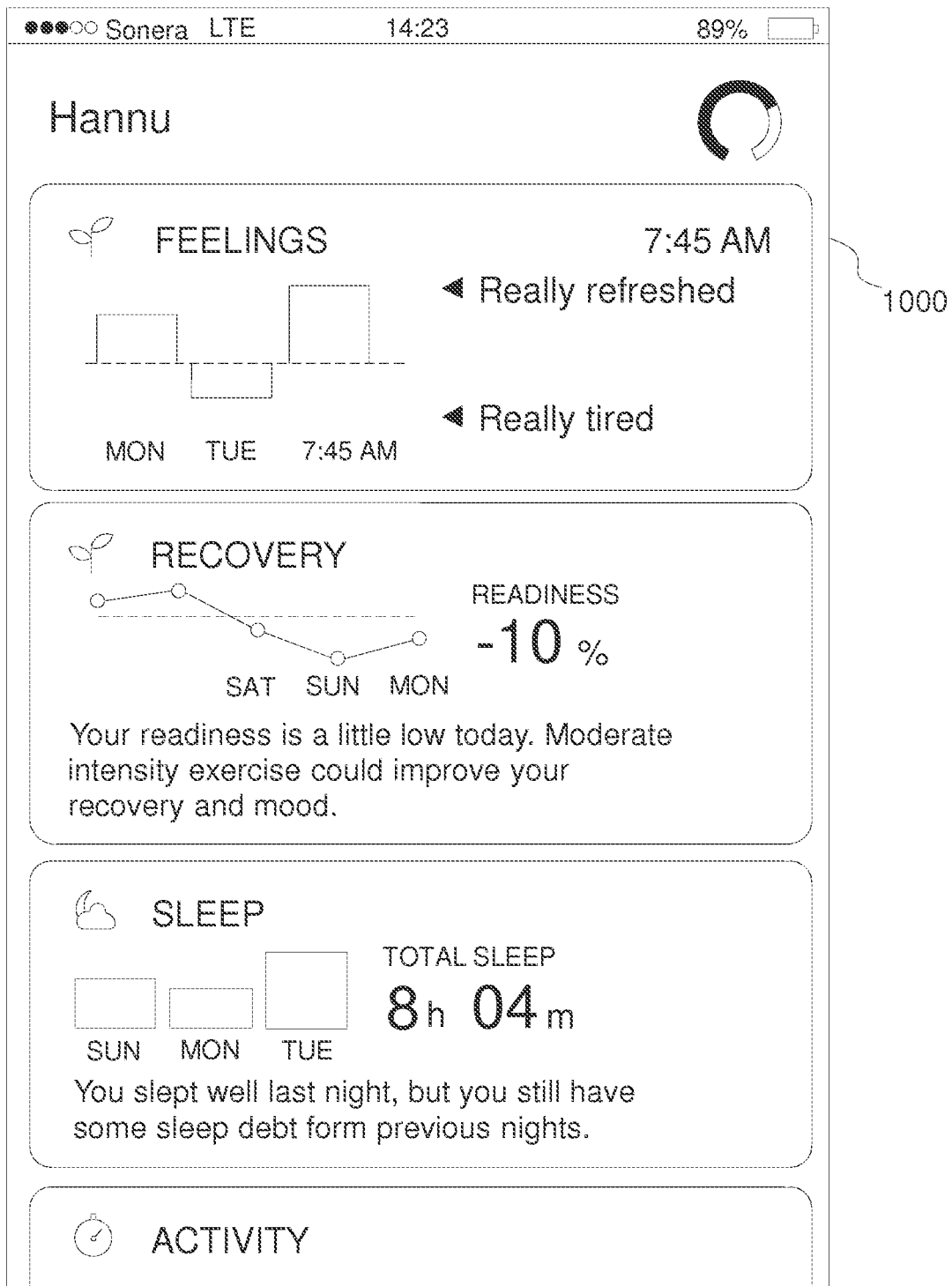

FIG. 10 shows another user interface 1000 rendered on the mobile communication device. Specifically, the UI 1000 shows a summary report for a user (for example Hannu) for both mental and physical changes as trends. The UI 1000 provides correlation of physiology, behavior and subjective feedback on feelings. For example, the UI 1000 provides trend of feelings (i.e. how the user has been feeling since last couple of days—Mon, Tue and today). Also, the UI 1000 provides information about performance against and recovery from prolonged stress. As shown, the UI 1000 provides a current readiness score (i.e. "Readiness—10%") and an instruction "Your readiness is a little low today. Moderate intensity exercise could improve your readiness and mood". The UI 1000 also provides a readiness score trend based on past days. Further, the UI 1000 provides a sleeping trend (current and past sleeping data) and a comment based on the sleeping trend. For example, the UI 1000 shows that the user slept for 8 hr 4 min on Tuesday night and the comment "You slept well last night, but you still have some sleep debt form previous nights".

Figure 11:
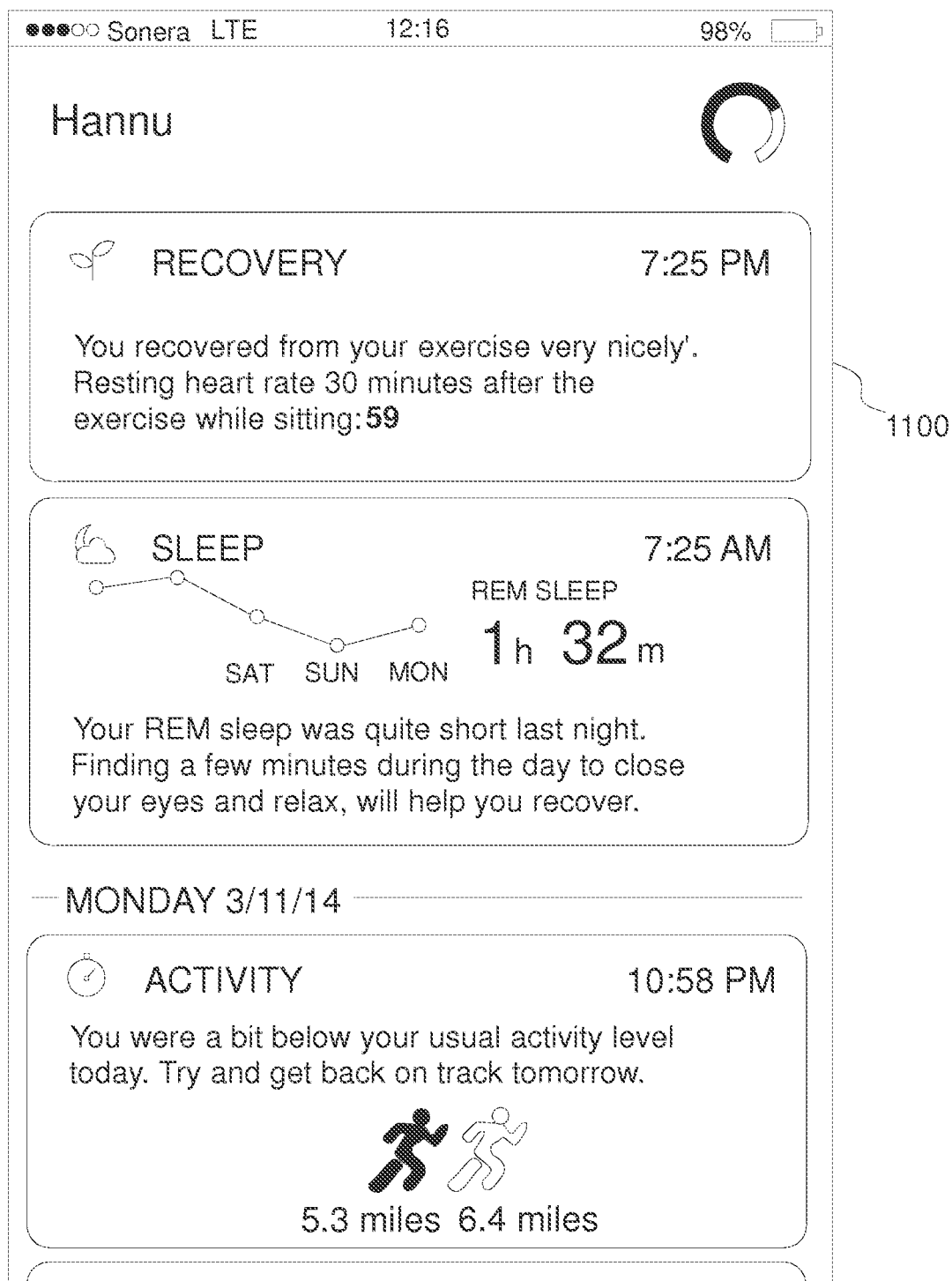

FIG. 11 shows yet another user interface 1100 rendered on the mobile communication device. Specifically, the UI 1100 is associated with proposals for the user, which can help the user to understand what affects physiology and feelings of the user and what the user can do to improve them. As shown, the UI 1100 provides an appropriate instruction (or proposal) associated with recovery of the user that may be after physical exercise, i.e. "You recovered from your exercise very nicely. Resting heart rate 30 minutes after the exercise while sitting: 59". Also, the UI 1100 provides an appropriate instruction associated with sleep of the user, i.e. "Your REM sleep was quite short last night. Finding a few minutes during the day to close your eyes and relax, will help you recover". Further, the UI 1100 provides an appropriate instruction associated with physical activity of the user, i.e. "You were a bit below your usual activity level today. Try and get back on track tomorrow".

Figure 12:
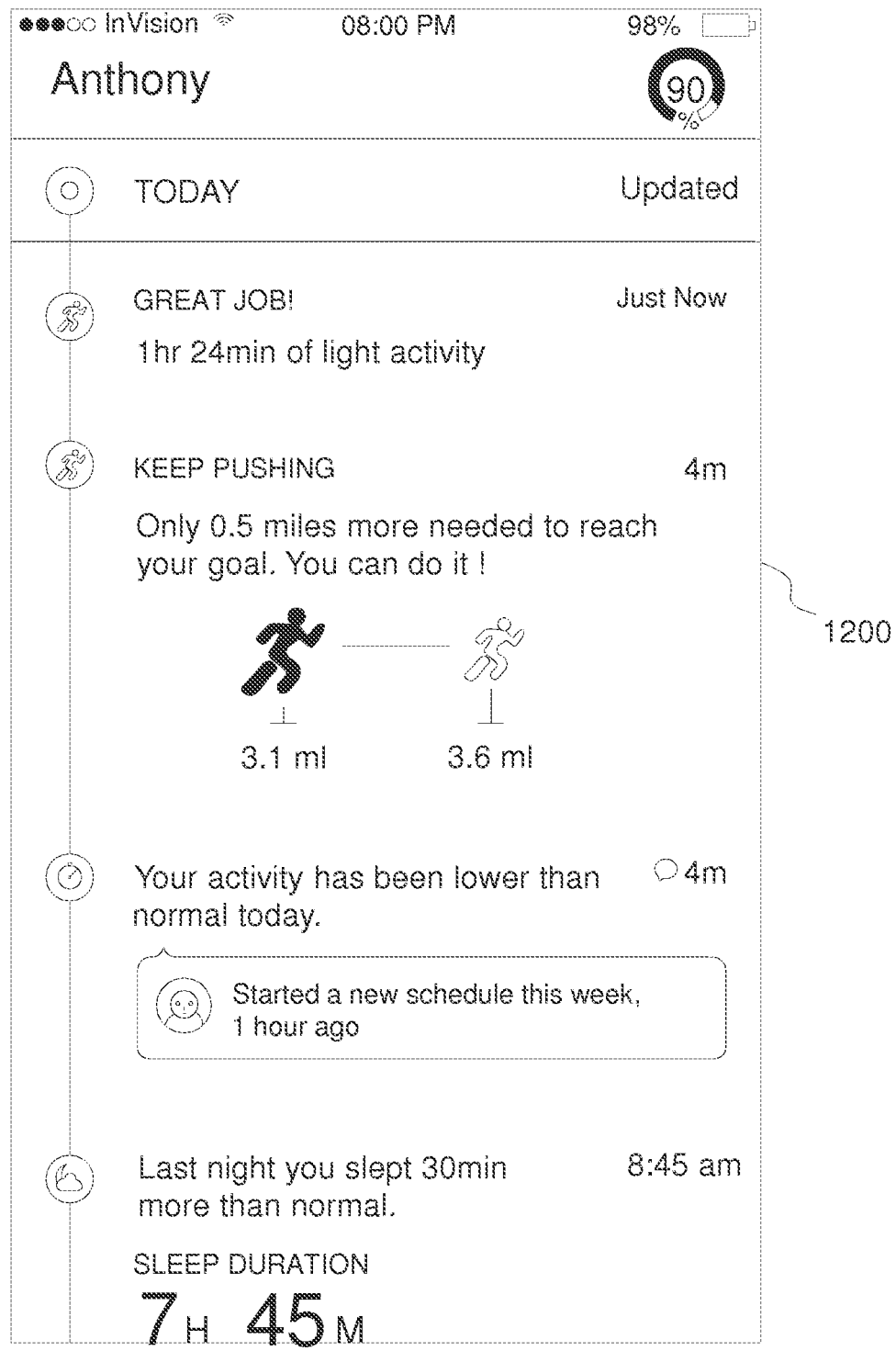

FIG. 12 shows another user interface 1200 rendered on the mobile communication device. Specifically, the UI 1200 is associated with updates of a particular day for a user (Anthony). As shown, the UI 1200 provides a latest update (just now) about physical activity, i.e. "GREAT JOB! 1 hr 24 min of light activity". Also, the UI 1200 provides a past update (4 m before) about the physical activity, i.e. "KEEP PUSHING—Only 0.5 miles more needed to reach your goal. You can do it!". The UI 1200 also include past update (4 m before) about user's feedback regarding the physical activity, i.e. "Started a new schedule this week, 1 hour ago". The UI 1200 also includes an old update (at 8:45 am) about the user sleep, i.e. "Last night you slept 30 min more than normal Sleep duration 7 hr 45 min. Additionally, the user interface 1200 depicts the readiness score of the user, i.e. about 90%.

Figure 13:
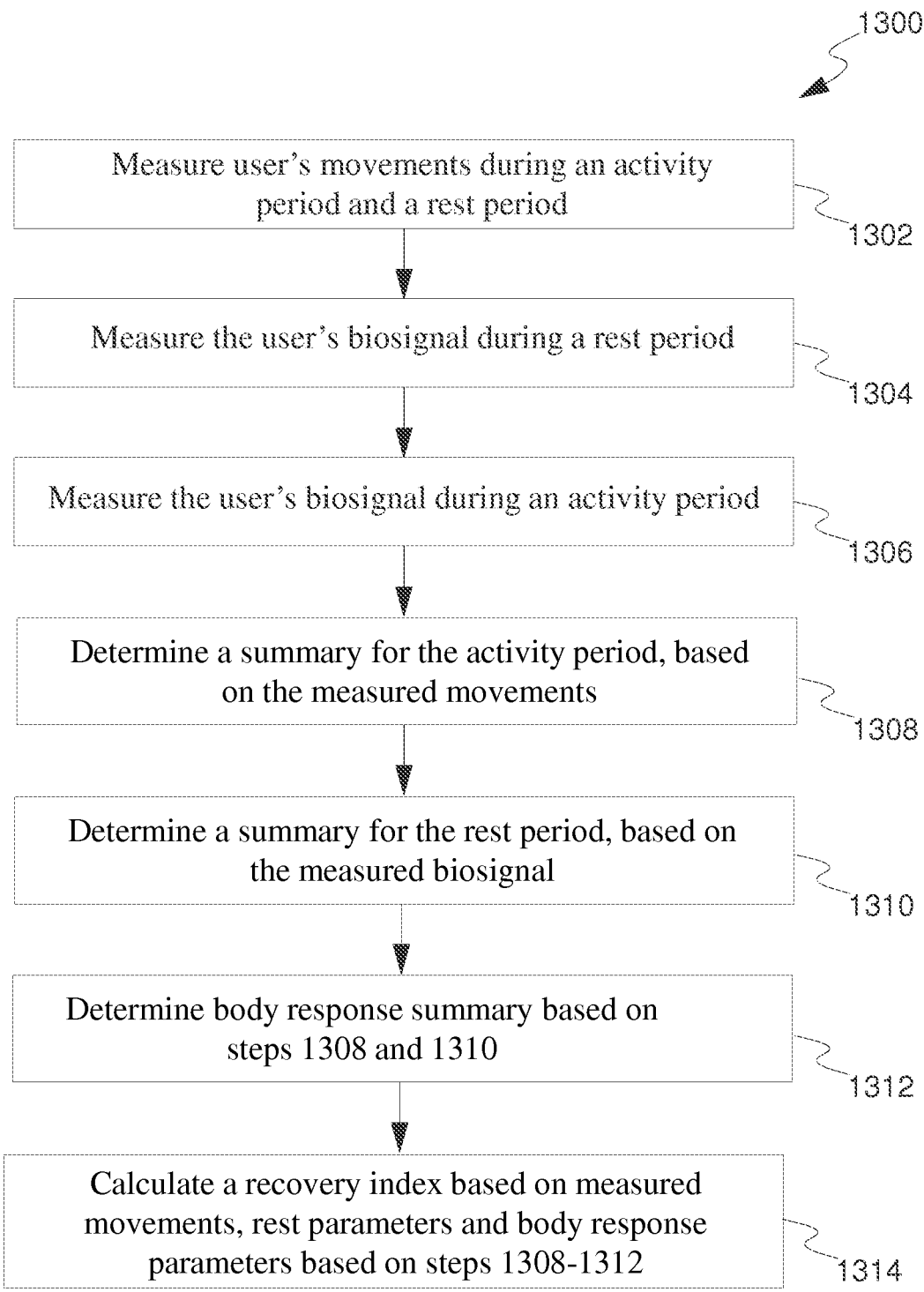
FIG. 13 is an illustration of steps of a method for assessing readiness of a user, in accordance with an embodiment of the present disclosure.

Referring now to FIG. 13, illustrated are steps of a method 1300 for assessing readiness of a user, in accordance with an embodiment of the present disclosure. Specifically, the method 1300 illustrates the steps for assessing readiness of a user using the system 100, explained in conjunction with the FIGS. 1-12.

At step 1302, the user's movements is measured during an activity period and a rest period.

At step 1304, the user's biosignal (at least one) is measured during a rest period. The biosignal may be for example derived as explained below in connection with FIG. 15. At an optional step 1306, the user's biosignal (at least one) is measured during an activity period. It is to be understood that step 1302 and the optional step 1306 are typically performed simultaneously.

The method may also comprise a step where various features are generated based on the measured biosignals. The features include for example IBI and heart rate and their distribution, zero crossing parameters and their distribution, autocorrelation parameters, amplitude variation and its distribution, and so on.

At step 1308, a summary for the activity period is determined, based on the measured movements.

At step 1310, a summary for the rest period is determined, based on the measured biosignal. Thereafter, in step 1312, a body response summary is determined, based on steps 1308 and 1310. It is to be understood that steps 1308 and 1310 can be performed in either order or simultaneously.

At step 1314, a readiness score is calculated based on the measured movements, and body response parameters based on steps 1308-1312, whereby the readiness score indicates a level of readiness of the user.

The steps 1302 to 1314 are only illustrative and other alternatives can also be provided where one or more steps are added, one or more steps are removed, or one or more steps are provided in a different sequence without departing from the scope of the claims herein. For example, the method 1300 may further include providing the user with appropriate instructions, related to at least one of physical activity and mental activity, for improving the user's readiness score. Also, the method 1300 may include using also historical data of the user to calculate the readiness score.

Figure 14:
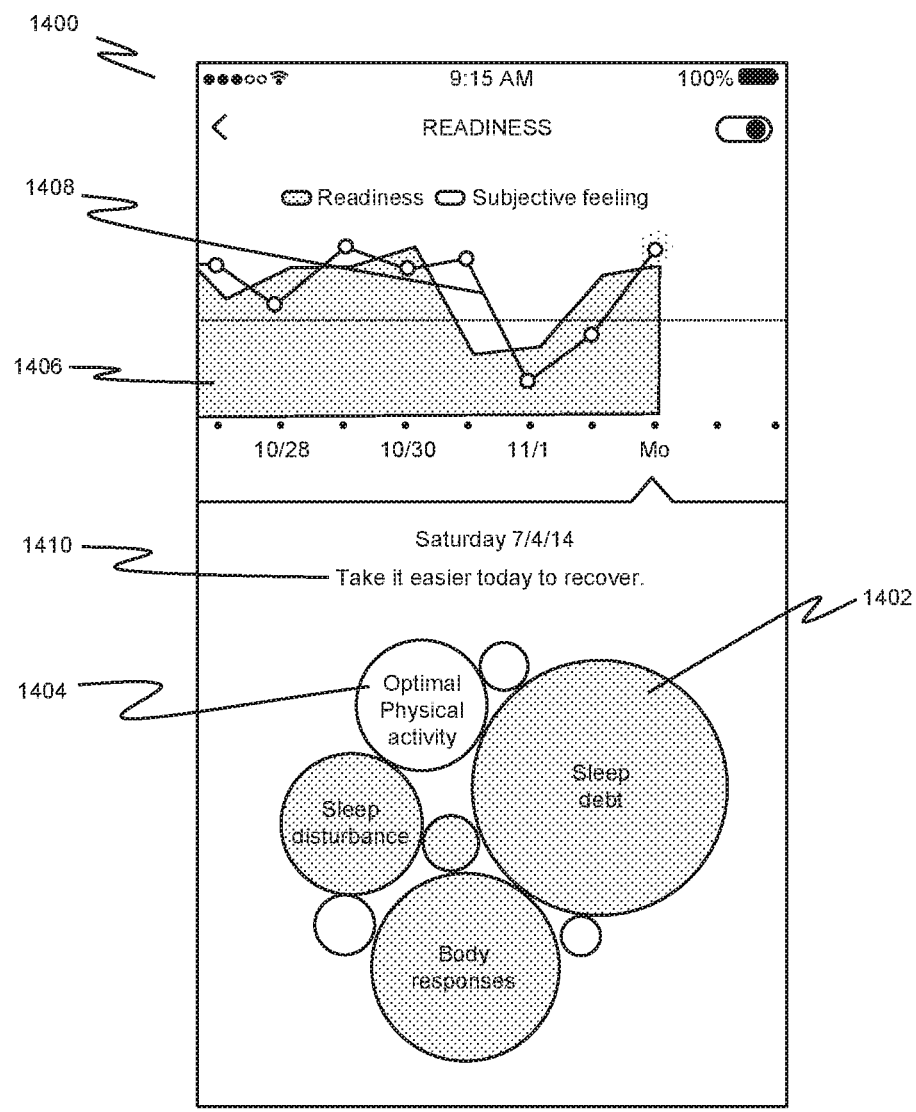
FIG. 14 is a further schematic illustration of a user interface in accordance with an embodiment of the present disclosure.

FIG. 14 is a further schematic illustration of a user interface in accordance with an embodiment of the present disclosure. The user interface 1400 is rendered on a mobile communication device. Specifically, the upper part of the UI 1400 is associated with a readiness of the user summarizing data over several days. The readiness graph 1406 may also be compared to subjective feelings 1408 that are collected based on user input. Readiness is a sum of the measured or estimated physical and mental resources that are in ideal case scaled according to the user's own norms. As shown, the UI 1410 may also express the readiness of each day as a main proposal associated with it, e.g. "Take it easier today to recover" given on Saturday 7/4/14. The lower part of the UI displays graphically the negative 1402 and positive 1404 contributors for readiness on each day. The size of the graphical obstacles represents their significance (magnitude or severity), and the color (intensity) represents positive or negative sign. Negative contributors can be e.g. sleep debt assessed over several nights 1402, sleep disturbance of previous night or abnormal body responses e.g. higher than typical night time heart rate. Importantly, on each day there can be both positive and negative contributors that may at least partially compensate for each other. Positive contributors can be e.g. optimal physical activity on the previous days 1404.

Figure 15:
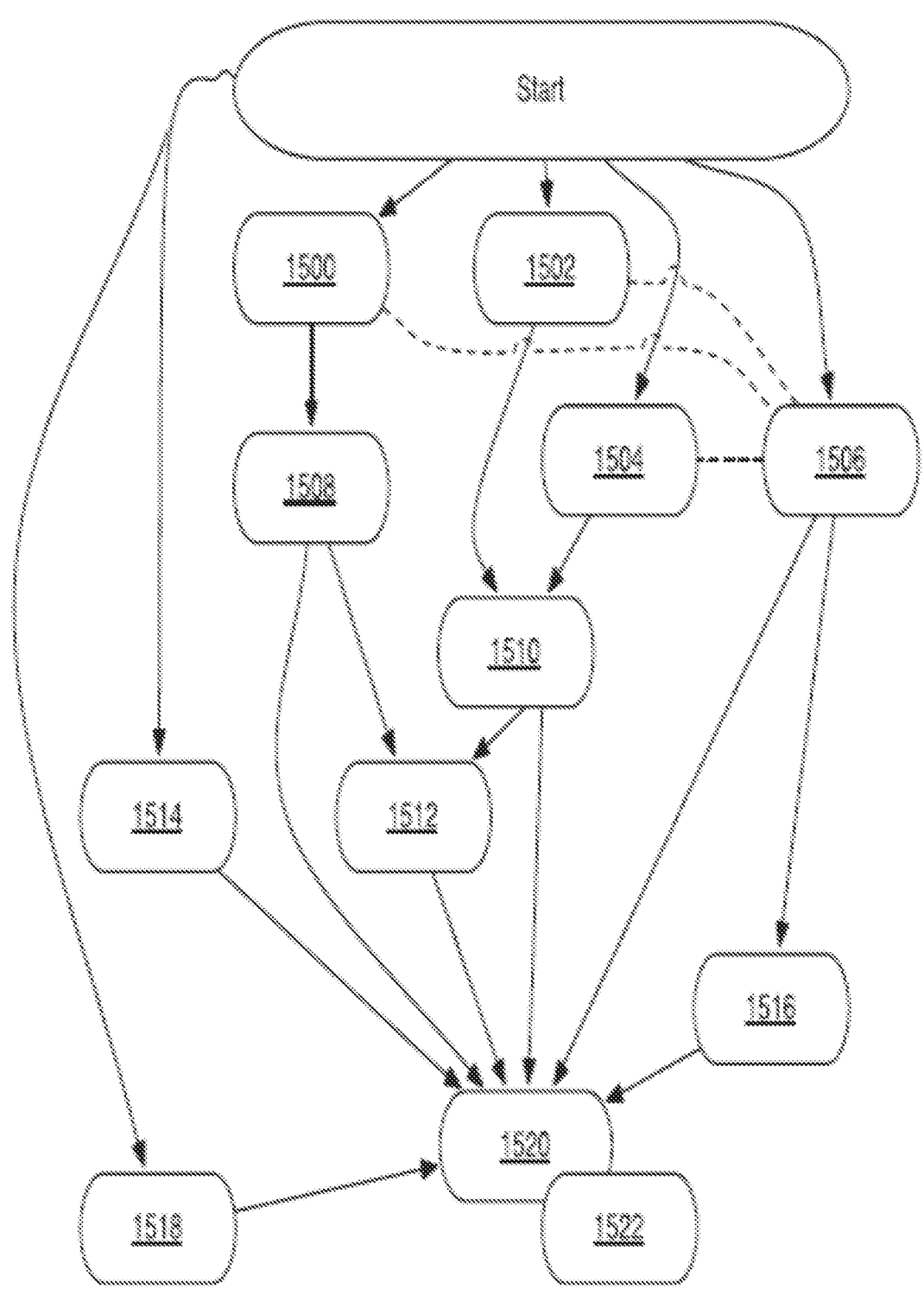
FIG. 15 is an illustration of steps of a method in accordance with a further embodiment of the present disclosure.

FIG. 15 is an illustration of steps of a method in accordance with a further embodiment of the present disclosure. In step 1500, movement data is measured during an activity period (in practice with an accelerometer, gyroscope, etc. or alternatively from a motion artifact of a biosignal such as an electrocardiogram (EKG), a PPG, an electromyogram (EMG), or data from global positioning system (GPS)). In an alternative step 1502, movement data is measured during a rest period (in practice with an accelerometer, gyroscope, etc. or alternatively from a motion artifact of a biosignal such as EKG, PPG, EMG). In a yet alternative step 1504, corresponding to a preferred case, also a biosignal (EKG, PPG, EMG, an electrodermal activity (EDA)) or another measurement associated with breathing (for example a breathing rate with impedance measurement or termistor, sensor attached to bed, microphone, video recording) is measured. In a still further alternative step 1506, which is also preferred, the user's subjective input on prevailing feelings is requested via a series of questions. The questionnaire may be synched to watch-time, rise-time, or start or end times of certain activity or rest parameters as determined based on steps 1500-1504. All of these steps can be performed either simultaneously or in sequence, as the case may be.

In step 1508, based on the results of step 1500, an activity summary for the day is determined, including one or more of the following: active time, steps, distance, energy expenditure, training impact/load, distribution of intensity/speed/step rate, time of activity in respect to bedtime, etc. If need be, results from any of the other steps can also be used for this determination. In step 1510, based on the steps 1502-1504, a rest summary for the night is determined, including one or more of the following: bedtime, rise time, total sleep duration, sleep disturbances, hypnogram, lowest hear rate, average heart rate, biosignal amplitude variation, heart rate variability, restlessness etc.

In step 1512 and based on steps 1508-1510, a body response summary for day to night, or activity period to rest period, is determined. The body response parameters may be e.g. training impact vs. heart rate recovery speed, daily physical activity parameter vs. amount of deep sleep or lowest heart rate of the night. The body response may also be changes in body signal as a response from rest to stand-up at rise time as determined based on steps 1500-1504.

In step 1514 and based on the user's history, a distribution of parameter in activity and rest summary is calculated, in order to use them as user dependent reference values (e.g. mean, standard deviation, percentiles). In step 1516, subjective feelings are correlated with activity and rest summary parameters over different time constants and delays in order to find user dependent reference values that can be described e.g. with words as sub-optimal or optimal. In a further step 1518, based on the user's own data (history database) activity or rest parameters are correlated with the following days' activity or rest parameters or readiness scores in order to provide supportive feedback how user has earlier managed to recover from challenging situations.

In step 1520 and based on steps 1506-1518, the relevance/significance for each activity and rest parameter is correlated in respect to estimated readiness using the user-independent and user-dependent scales. Finally, in step 1522 and based on steps 1506-1518, the relevance of a number of predetermined textual advice is computed, and the most relevant of them is selected.

Figure 16:
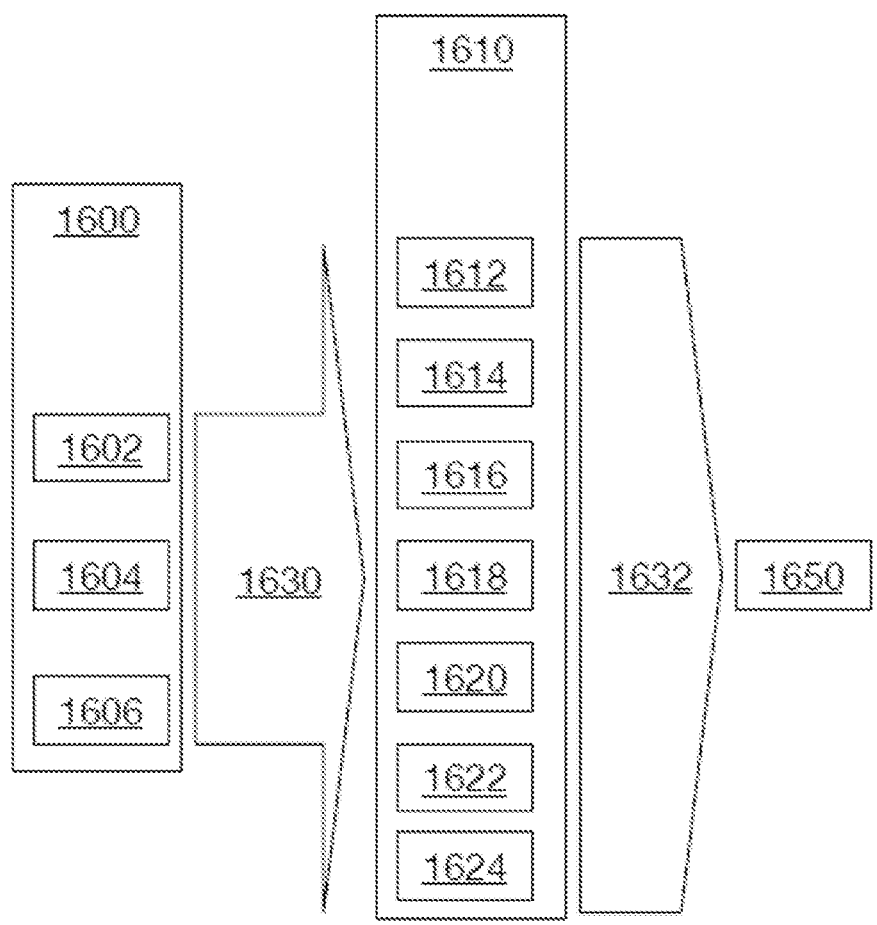
FIG. 16 is an illustration of steps of a method in accordance with a further embodiment of the present disclosure.

FIG. 16 is an illustration of steps for calculating readiness score 1650 for a user. In a first step set of parameters is measured with a ring 1600. The ring is configured to measure heart rate (HR) 1602, body temperature 1604 and activity 1606. Accelerometer is used to measure the activity 1606. IR is used to measure heart rate (HR) 1062. Temperature 1604 is measured with temperature sensor. The temperature 1604 refers to body temperature of the user.

Sub parameters 1610 are calculated using the measured parameters using algorithm 1630. Sub parameters 1610 include sleeping times of previous three nights. Sleeping time of last night is 1612, sleeping time of night before last night is 1614 and sleeping time of two nights before last night is 1616. Sub parameters further include activity level parameter 1 1618 and activity level parameter 2 1620. Further sub parameters include first heart rate parameter 1622 and second heart rate parameter 1624. The sub parameters 1610 are used by second algorithm to determine readiness score 1650.

Figure 17:
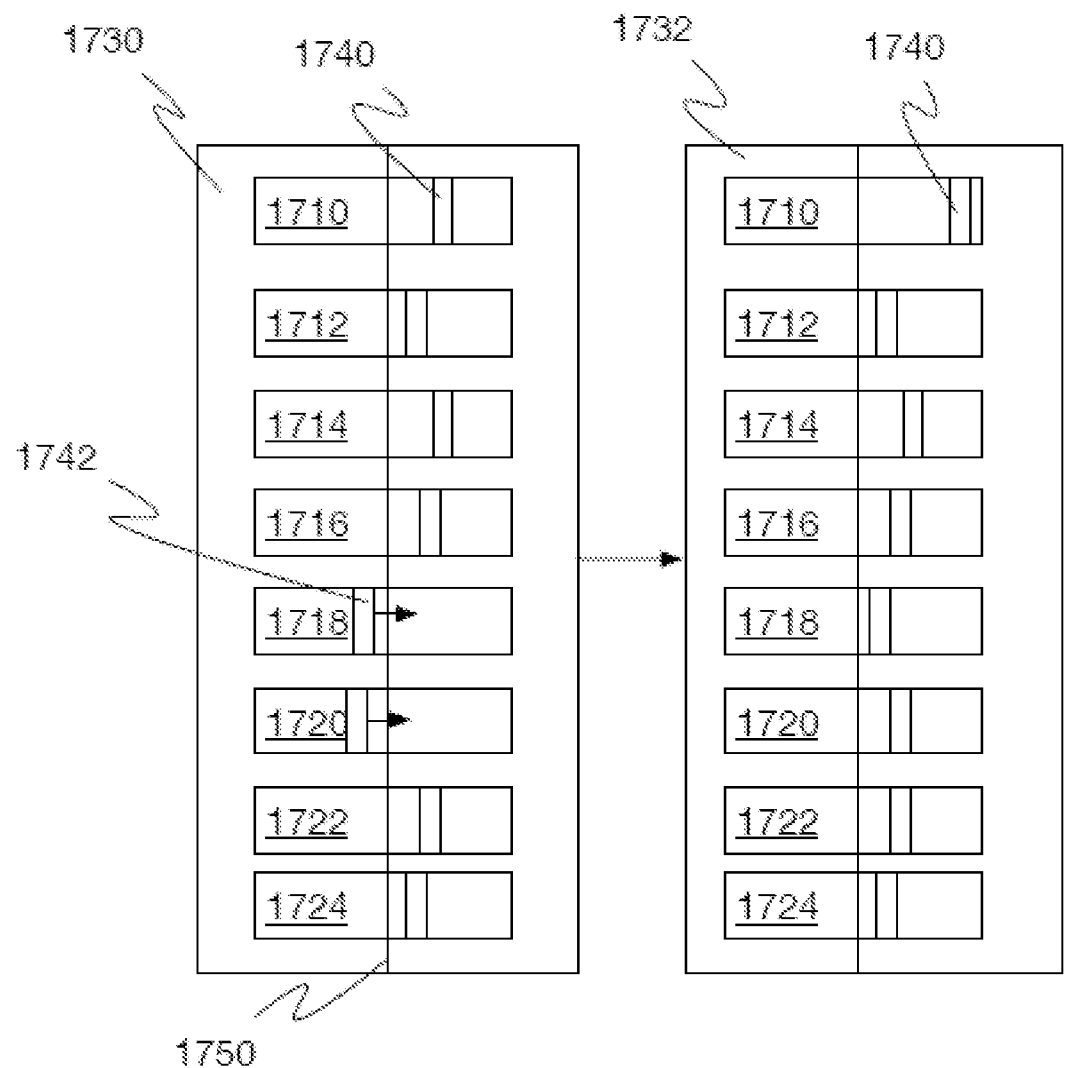
FIG. 17 is an illustration of an exemplary user interface.

FIG. 17 is an illustration of user interface view 1730. The view 1730 has indication 1750 for indicating neutral value. Values left from the neutral value are considered as negative values and values from right are considered as positive values. According embodiments user view 1730 can be configured also to show negative values can be in right and positive in left. Readiness score is rendered to user in area 1710. The value of the readiness score is indicated with a graphical element 1740. Sub parameter values related to sleep of previous nights, heart rate, activity, temperature are rendered in the areas 1710, 1712, 1714, 1716, 1718, 1720, 1722, 1724. Value is indicated with slider bar 1742.

Based on embodiment user can use pointer such as finger to move slider bar 1742 to simulate readiness score value 1740 as shown in user view 1732. In an example user has selected to drag slider bar 1742 of areas 1718 and 1720 (in present example activity 1 and activity 2) to direction indicated with arrow to simulate effect of adding more activities to the day. The user can see in the user view 1732 that the recover index shows more positive sign if the user adds activities (such as moving).

FIG. 18A, FIG. 18B and FIG. 18C are illustrations of alternative user interface views 1800, 1802, 1804 respectively. The user interfaces show readiness value 1810 and positively affecting sub parameters 1830 and negatively affecting sub parameters 1820. User interface can be further configured to indicate trend of the readiness by animations or arrows or similar. The user interface can be in addition configured to enable user to test impact of each sub parameters for the readiness value.

Further different colors can be used for differentiating "plus or minus" values. For example green has a positive meaning and red a negative one. Colors and left-right bars can be used also together to visualize and emphasize different parameter values and their contribution. Also different shades of colors can be used. The shade can be darker or lighter if a parameter value is higher or lower.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for assessing readiness of a user, the method comprising:
    obtaining the user's movements;
    using the obtained user's movements to determine a nature of the period, wherein the nature of the period is selected from an activity period and a rest period;
    measuring at least one biosignal of the user during the rest period;
    determining a rest summary for the rest period, based on the measured at least one biosignal and at least one biosignal of a previous rest period;

determining an activity summary for the activity period, based on the obtained movements of an activity period and obtained movements of at least one previous activity period;
determining a body response summary based on the rest summary and the activity summary;
calculating a readiness score based on the body response summary and a previous body response summary, whereby the readiness score indicates a level of readiness of the user; and
using a user interface of the mobile communication device to show elements contributing to the readiness score and instructions related to physical activity and mental activity for improving the readiness score.

2. A method according to claim 1, wherein obtaining the user's movements is performed by measuring the user's movements or by retrieving the user's movement data from a separate device.

3. A method according to claim 1, further comprising measuring at least one biosignal during the activity period.

4. A method according to claim 1, wherein the at least one biosignal is selected from the group consisting of an electrocardiogram, a photoplethysmogram, an electromyogram, an electroocylogram, a heart rate, a heart rate variability, a body temperature, a resting heart rate, an average heart rate and signals related to breathing.

5. A method according to claim 1, wherein determining the rest summary comprises at least one of determining a sleep factor, determining a sleep balance, determining lowest body temperature during rest and determining a resting heart rate.

6. A method according to claim 1, further comprising providing the user with appropriate instructions, related to at least one of physical activity, mental activity and rest, for improving the user's readiness score.

7. A method according to claim 1, further comprising using medical history of the user to calculate the readiness score.

8. A system for assessing readiness of a user, the system comprising:
a ring configured to be worn by the user and comprising means for measuring at least one biosignal of the user during a rest period,
a mobile communication device configured to communicate with the ring,
means for measuring the user's movements during an activity period and the rest period, and
a server configured to communicate with the mobile communication device, the server being operable to
use the measured user's movements to determine a nature of the period, wherein the nature of the period is selected from the activity period and the rest period,
determine a rest summary for the rest period, based on the measured at least one biosignal and at least one biosignal of a previous rest period,
determine an activity summary for the activity period, based on the measured movements and measured movements of at least one previous activity period,
determine a body response summary based on the rest summary and the activity summary; and
calculate a readiness score based on the body response summary and a previous body response summary, whereby the readiness score indicates a level of readiness of the user; and
a user interface of the mobile communication device configured to show elements contributing to the readiness score and instructions related to physical activity and mental activity for improving the readiness score.

9. A system according to claim 8, wherein the means for measuring the user's movements are arranged on the ring, in the mobile communication device or in an activity determination device.

10. A system according to claim 8, wherein the mobile communication device is configured to visually present the readiness score to the user.

11. A system according to claim 8, wherein the means for measuring the user's movements is selected from the group consisting of an accelerometer, a gyroscope and a magnetic field sensor.

12. A system according to claim 8, wherein the means for measuring at least one biosignal comprises a photon source arranged on the inner surface of the ring and a photon detector arranged on the inner surface of the ring.

13. A system according to claim 8, wherein the ring further comprises a first electrode and a second electrode adapted to measure an electrocardiogram.

* * * * *

Disclaimer

10,842,429 B2 - Hannu Kinnunen, Oulu (FI); Harri Laakkonen, Oulu (FI); Kari Kivalä, Helsinki (FI); Ashley Colley, Rovaniemi (FI); Petteri Lahtela, Jääli (FI); Markku Koskela, Oulu (FI); Heidi Jurvelin, Oulu (FI). METHOD AND SYSTEM FOR ASSESSING A READINESS SCORE OF A USER. Patent dated November 24, 2020. Disclaimer filed October 30, 2024, by the assignee, Oura Health Oy.

I hereby disclaim the following complete Claims 1-6 of said patent.

*(Official Gazette, December 10, 2024)*